US008435538B2

(12) United States Patent
Kakkar et al.

(10) Patent No.: US 8,435,538 B2
(45) Date of Patent: May 7, 2013

(54) ANTI-ATHEROMA VACCINE

(75) Inventors: Vijay Kakkar, London (GB); Xinjie Lu, London (GB)

(73) Assignee: Thrombosis Research Institute, London (GB)

( * ) Notice: Subject to any disclaimer, the term of this patent is extended or adjusted under 35 U.S.C. 154(b) by 31 days.

(21) Appl. No.: 12/937,235

(22) PCT Filed: Apr. 14, 2009

(86) PCT No.: PCT/GB2009/050366
§ 371 (c)(1),
(2), (4) Date: Nov. 5, 2010

(87) PCT Pub. No.: WO2009/125231
PCT Pub. Date: Oct. 15, 2009

(65) Prior Publication Data
US 2011/0045012 A1    Feb. 24, 2011

(30) Foreign Application Priority Data

Apr. 10, 2008  (GB) .................................. 0806461.0
Apr. 25, 2008  (GB) .................................. 0807579.8

(51) Int. Cl.
*A61K 39/385*    (2006.01)
*C07K 14/00*    (2006.01)

(52) U.S. Cl.
USPC .................... 424/192.1; 424/185.1; 530/300; 530/350

(58) Field of Classification Search ........................ None
See application file for complete search history.

(56) References Cited

U.S. PATENT DOCUMENTS 7,498,046 B2 *   3/2009   Wang et al. .................... 424/520
7,544,360 B2 *   6/2009   Nilsson et al. ............. 424/185.1

FOREIGN PATENT DOCUMENTS

| WO | WO 97/41227 | 11/1997 |
| WO | WO 98/42834 | 10/1998 |
| WO | WO 01/68119 | 9/2001 |
| WO | WO 2006/072888 | * 7/2006 |

OTHER PUBLICATIONS

International Preliminary Report on Patentability in PCT/GB2009/050366, dated Oct. 12, 2010 (10 pages).
Choi, et al. "Establishment of *Porphyomonas gingivalis* Heat-Shock-protein-specific T-cell Lines from Atherosclerosis Patients," *J. Dent. Res.*, 81(5):344-348 (2002).

* cited by examiner

*Primary Examiner* — Padma V Baskar
(74) *Attorney, Agent, or Firm* — Klarquist Sparkman, LLP

(57) ABSTRACT

The invention relates to a recombinant protein comprising: a carrier portion; a first epitope capable of eliciting an anti-atheroma response; and a second epitope capable of eliciting an anti-atheroma response, characterized in that said first and second epitopes are distinct from one another.

15 Claims, 9 Drawing Sheets

Figure 1:
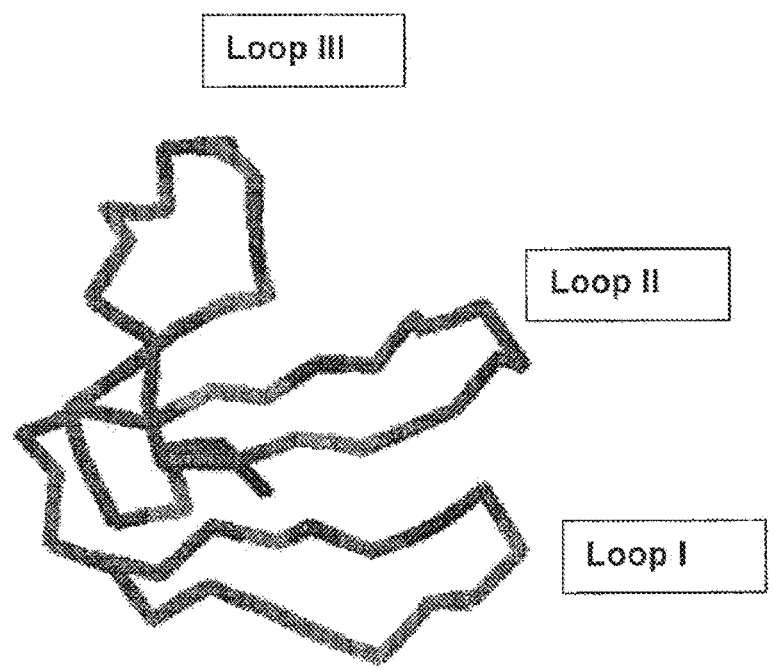

V7: PDGF-loop III in dendroaspin-loop II
and CMV in dendroaspin-loop III

```
                        SEQUENCE LISTING

<160> NUMBER OF SEQ ID NOS: 40

<210> SEQ ID NO 1
<211> LENGTH: 9
<212> TYPE: PRT
<213> ORGANISM: Homo sapiens

<400> SEQUENCE: 1

Arg Lys Ile Glu Ile Val Arg Lys Lys
1               5

<210> SEQ ID NO 2
<211> LENGTH: 9
<212> TYPE: PRT
<213> ORGANISM: Homo sapiens
<220> FEATURE:
<221> NAME/KEY: ACETYLATION
<222> LOCATION: (1)..(1)
<220> FEATURE:
<221> NAME/KEY: ACETYLATION
<222> LOCATION: (1)..(1)
<223> OTHER INFORMATION: Modified PDGF B chain

<400> SEQUENCE: 2

Arg Lys Ile Glu Ile Val Arg Lys Lys
1               5

<210> SEQ ID NO 3
<211> LENGTH: 9
<212> TYPE: PRT
<213> ORGANISM: Homo sapiens
<220> FEATURE:
<221> NAME/KEY: ACETYLATION
<222> LOCATION: (1)..(1)
<220> FEATURE:
<221> NAME/KEY: ACETYLATION
<222> LOCATION: (1)..(1)
<223> OTHER INFORMATION: Modified PDGF B chain
<220> FEATURE:
<221> NAME/KEY: AMIDATION
<222> LOCATION: (9)..(9)

<400> SEQUENCE: 3

Arg Lys Ile Glu Ile Val Arg Lys Lys
1               5

<210> SEQ ID NO 4
<211> LENGTH: 10
<212> TYPE: PRT
<213> ORGANISM: Artificial
<220> FEATURE:
<223> OTHER INFORMATION: Modified PDGF B chain

<400> SEQUENCE: 4

Arg Lys Ile Glu Ile Val Arg Lys Lys Cys
```

```
1               5                   10

<210> SEQ ID NO 5
<211> LENGTH: 10
<212> TYPE: PRT
<213> ORGANISM: Artificial
<220> FEATURE:
<223> OTHER INFORMATION: Modified PDGF B chain
<220> FEATURE:
<221> NAME/KEY: ACETYLATION
<222> LOCATION: (1)..(1)
<220> FEATURE:
<221> NAME/KEY: ACETYLATION
<222> LOCATION: (1)..(1)
<223> OTHER INFORMATION: Modified PDGF B chain

<400> SEQUENCE: 5

Arg Lys Ile Glu Ile Val Arg Lys Lys Cys
1               5                   10

<210> SEQ ID NO 6
<211> LENGTH: 10
<212> TYPE: PRT
<213> ORGANISM: Artificial
<220> FEATURE:
<223> OTHER INFORMATION: Modified PDGF B chain

<400> SEQUENCE: 6

Ile Val Arg Lys Arg Cys Arg Lys Ile Glu
1               5                   10

<210> SEQ ID NO 7
<211> LENGTH: 10
<212> TYPE: PRT
<213> ORGANISM: Artificial
<220> FEATURE:
<223> OTHER INFORMATION: Modified PDGF B chain, cyclic

<400> SEQUENCE: 7

Ile Val Arg Lys Arg Cys Arg Lys Ile Glu
1               5                   10

<210> SEQ ID NO 8
<211> LENGTH: 18
<212> TYPE: PRT
<213> ORGANISM: Artificial
<220> FEATURE:
<223> OTHER INFORMATION: Modified PDGF B chain, cyclic

<400> SEQUENCE: 8

Gly Gly Ile Ser Arg Arg Leu Ile Asp Arg Thr Asn Ala Asn Phe Leu
1               5                   10                  15

Cys Gly

<210> SEQ ID NO 9
<211> LENGTH: 10
<212> TYPE: PRT
<213> ORGANISM: Mycobacterium bovis

<400> SEQUENCE: 9

Pro Lys Gly Arg Asn Val Val Leu Glu Lys
1               5                   10

<210> SEQ ID NO 10
<211> LENGTH: 10
<212> TYPE: PRT
<213> ORGANISM: Mycobacterium bovis
```

```
<400> SEQUENCE: 10

Thr Val Leu Ala Gln Ala Leu Val Arg Glu
1               5                   10

<210> SEQ ID NO 11
<211> LENGTH: 10
<212> TYPE: PRT
<213> ORGANISM: Mycobacterium bovis

<400> SEQUENCE: 11

Gln Ile Ala Ala Thr Ala Ala Ile Ser Ala
1               5                   10

<210> SEQ ID NO 12
<211> LENGTH: 10
<212> TYPE: PRT
<213> ORGANISM: Mycobacterium bovis

<400> SEQUENCE: 12

Arg Phe Asp Lys Gly Tyr Ile Ser Gly Tyr
1               5                   10

<210> SEQ ID NO 13
<211> LENGTH: 10
<212> TYPE: PRT
<213> ORGANISM: Mycobacterium bovis

<400> SEQUENCE: 13

Tyr Ile Ser Gly Tyr Phe Val Thr Asp Pro
1               5                   10

<210> SEQ ID NO 14
<211> LENGTH: 10
<212> TYPE: PRT
<213> ORGANISM: Mycobacterium bovis

<400> SEQUENCE: 14

Phe Val Thr Asp Pro Glu Arg Gln Glu Ala
1               5                   10

<210> SEQ ID NO 15
<211> LENGTH: 10
<212> TYPE: PRT
<213> ORGANISM: Mycobacterium bovis

<400> SEQUENCE: 15

Tyr Ile Leu Leu Val Ser Ser Lys Val Ser
1               5                   10

<210> SEQ ID NO 16
<211> LENGTH: 10
<212> TYPE: PRT
<213> ORGANISM: Mycobacterium bovis

<400> SEQUENCE: 16

Pro Gly Phe Gly Asp Arg Arg Lys Ala Met
1               5                   10

<210> SEQ ID NO 17
<211> LENGTH: 10
<212> TYPE: PRT
<213> ORGANISM: Mycobacterium bovis

<400> SEQUENCE: 17

Arg Arg Lys Ala Met Leu Gln Asp Met Ala
```

```
                  1               5                   10
```

<210> SEQ ID NO 18
<211> LENGTH: 10
<212> TYPE: PRT
<213> ORGANISM: Mycobacterium bovis

<400> SEQUENCE: 18

```
Leu Ala Lys Leu Ala Gly Gly Val Ala Val
1               5                   10
```

<210> SEQ ID NO 19
<211> LENGTH: 10
<212> TYPE: PRT
<213> ORGANISM: Mycobacterium bovis

<400> SEQUENCE: 19

```
Gly Val Thr Leu Leu Gln Ala Ala Pro Thr
1               5                   10
```

<210> SEQ ID NO 20
<211> LENGTH: 10
<212> TYPE: PRT
<213> ORGANISM: Mycobacterium bovis

<400> SEQUENCE: 20

```
Asn Ala Ala Ser Ile Ala Gly Leu Phe Leu
1               5                   10
```

<210> SEQ ID NO 21
<211> LENGTH: 10
<212> TYPE: PRT
<213> ORGANISM: Mycobacterium bovis

<400> SEQUENCE: 21

Ala Gly Leu Phe Leu Thr Thr Glu Ala Val
1 5 10

<210> SEQ ID NO 22
<211> LENGTH: 14
<212> TYPE: PRT
<213> ORGANISM: Homo sapiens

<400> SEQUENCE: 22

Ile Ser Arg Arg Leu Ile Asp Arg Thr Asn Ala Asn Phe Leu
1 5 10

<210> SEQ ID NO 23
<211> LENGTH: 12
<212> TYPE: PRT
<213> ORGANISM: Streptococcus pneumoniae

<400> SEQUENCE: 23

Phe His Leu Pro Tyr Asn His Asn Trp Phe Ala Leu
1 5 10

<210> SEQ ID NO 24
<211> LENGTH: 9
<212> TYPE: PRT
<213> ORGANISM: Cytomegalovirus

<400> SEQUENCE: 24

Ala Gly Pro Pro Arg Tyr Ser Arg Ile
1 5

```
<210> SEQ ID NO 25
<211> LENGTH: 20
<212> TYPE: PRT
<213> ORGANISM: Homo sapiens

<400> SEQUENCE: 25

Ile Glu Ile Gly Leu Glu Gly Lys Gly Phe Glu Pro Thr Leu Glu Ala
1               5                   10                  15

Leu Phe Gly Lys
            20

<210> SEQ ID NO 26
<211> LENGTH: 11
<212> TYPE: PRT
<213> ORGANISM: Homo sapiens

<400> SEQUENCE: 26

Ala Glu Leu Lys Lys Gln Ser Lys Pro Val Thr
1               5                   10

<210> SEQ ID NO 27
<211> LENGTH: 9
<212> TYPE: PRT
<213> ORGANISM: Human cytomegalovirus

<400> SEQUENCE: 27

Asn Leu Val Pro Met Val Ala Thr Val
1               5

<210> SEQ ID NO 28
<211> LENGTH: 9
<212> TYPE: PRT
<213> ORGANISM: Homo sapiens

<400> SEQUENCE: 28

Pro Gly Phe Gly Asp Asn Arg Lys Asn
1               5

<210> SEQ ID NO 29
<211> LENGTH: 10
<212> TYPE: PRT
<213> ORGANISM: Homo sapiens

<400> SEQUENCE: 29

Val Gln Asp Val Ala Asn Asn Thr Asn Glu
1               5                   10

<210> SEQ ID NO 30
<211> LENGTH: 9
<212> TYPE: PRT
<213> ORGANISM: Human cytomegalovirus

<400> SEQUENCE: 30

Ser Val Asn Val His Asn Pro Thr Gly
1               5

<210> SEQ ID NO 31
<211> LENGTH: 84
<212> TYPE: PRT
<213> ORGANISM: Artificial
<220> FEATURE:
<223> OTHER INFORMATION: Synthetic peptide (partial CETP epitope and
      Porphyromonas hsp epitope in dendroaspin scaffold)

<400> SEQUENCE: 31

Met Asp Phe G

```
                1               5                  10                 15
Leu Ser Gly Gly Gly Gly Gly Arg Ile Cys Tyr Asn His Leu Gly Thr
                        20                 25                 30

Lys Pro Pro Thr Thr Glu Thr Cys Gln Glu Asp Ser Cys Tyr Lys Asn
                        35                 40                 45

Ile Trp Thr Phe Asp Asn Ile Ile Arg Arg Gly Cys Gly Cys Phe Thr
            50                 55                 60

Val Gln Asp Val Ala Asn Asn Thr Asn Glu Tyr Cys Cys Glu Ser Asp
65                  70                 75                 80

Lys Cys Asn Leu

<210> SEQ ID NO 32
<211> LENGTH: 18
<212> TYPE: PRT
<213> ORGANISM: Homo sapiens

<400> SEQUENCE: 32

Met Asp Phe Gly Phe Pro Glu His Leu Leu Val Asp Phe Leu Gln Ser
1               5                  10                 15

Leu Ser

<210> SEQ ID NO 33
<211> LENGTH: 15
<212> TYPE: PRT
<213> ORGANISM: Porphoryomonas gingivalis

<400> SEQUENCE: 33

Cys Phe Thr Val Gln Asp Val Ala Asn Asn Thr Asn Glu Tyr Cys
1               5                  10                 15

<210> SEQ ID NO 34
<211> LENGTH: 10
<212> TYPE: PRT
<213> ORGANISM: Homo sapiens

<400> SEQUENCE: 34

Pro Gly Phe Gly Asp Asn Arg Lys Asn Gln
1               5                  10

<210> SEQ ID NO 35
<211> LENGTH: 10
<212> TYPE: PRT
<213> ORGANISM: Porphyromonas gingivalis

<400> SEQUENCE: 35

Val Lys Glu Val Ala Ser Lys Thr Asn Asp
1               5                  10

<210> SEQ ID NO 36
<211> LENGTH: 16
<212> TYPE: PRT
<213> ORGANISM: Homo sapiens

<400> SEQUENCE: 36

Glu Gly Glu Ala Leu Ser Thr Leu Val Val Asn Lys Ile Arg Gly Thr
1               5                  10                 15

<210> SEQ ID NO 37
<211> LENGTH: 7
<212> TYPE: PRT
<213> ORGANISM: Chlamydia pneumoniae

<400> SEQUENCE: 37
```

```
Asp Tyr Val Phe Asp Arg Ile
1               5

<210> SEQ ID NO 38
<211> LENGTH: 9
<212> TYPE: PRT
<213> ORGANISM: Chlamydia pneumoniae

<400> SEQUENCE: 38

Gln Ala Val Ala Asn Gly Gly Ala Ile
1               5

<210> SEQ ID NO 39
<211> LENGTH: 15
<212> TYPE: PRT
<213> ORGANISM: Homo sapiens

<400> SEQUENCE: 39

Lys Thr Thr Lys Gln Ser Phe Asp Leu Ser Val Lys Ala Gln Tyr
1               5                   10                  15

<210> SEQ ID NO 40
<211> LENGTH: 26
<212> TYPE: PRT
<213> ORGANISM: Homo sapiens

<400> SEQUENCE: 40

Arg Asp Gly Phe Leu Leu Leu Gln Met Asp Phe Gly Phe Pro Glu His
1               5                   10                  15

Leu Leu Val Asp Phe Leu Gln Ser Leu Ser
            20                  25
```

ANTI-ATHEROMA VACCINE

CROSS REFERENCE TO RELATED APPLICATIONS

This is the U.S. National Stage of International Application No. PCT/GB2009/050366, filed Apr. 14, 2009, which was published in English under PCT Article 21(2), which in turn claims the benefit of GB Application No. 0806461.0, filed Apr. 10, 2008, and GB Application No. 0807579.8, filed Apr. 25, 2008.

FIELD OF INVENTION

The invention relates immunogenic and vaccine compositions comprising recombinant molecule presenting inserted epitopes from a variety of antigens. In particular, the invention relates to such compositions for eliciting an immune response against antigens and pathogens involved in the development of cardiovascular disease.

BACKGROUND OF THE INVENTION

Cardiovascular disease (CVD) has become a ubiquitous cause of death and disability, being responsible for almost 50% of all deaths. Heart attack (CHD) and stroke are two of its most important manifestations, others being occlusive peripheral vascular disease (PVD) and venous thromboembolism. CVD is now responsible for 51% of all deaths i.e. two and a half times more than all types of cancer (21%) put together.

Atheroma is a progressive disease best described according to the classification of the disease that has been made by the American Heart Association's Committee on Vascular Lesions (Stary et al. Arterioscler Thromb. 1994, 14, 840-856; Stary et al. Arterioscler Thromb Vasc Biol. 1995, 15, 1512-1531). The first identifiable lesion (type I) contains visible evidence of accumulated lipoprotein enough to engender an increase in resident macrophages and the formation of scattered lipid containing macrophages (foam cells). Type II lesions consist of larger accumulations of macrophage foam cells sandwiched between lipid-laden and proliferating smooth muscle cells—these are the lesions often designated as fatty streaks which may be observed in the artery wall from an early age. Type III lesions contain extracellular lipid droplets and other particles that may interfere with the coordinated behaviour of the layers of abnormally proliferating intimal smooth muscle cells. In type IV lesions (known therefrom as atheroma, since symptoms may occur), this extracellular lipid has coalesced into an increasingly disruptive core of free-floating lipid. In middle age, these start to contain thick layers of fibrous connective tissue (type V lesion) and to exhibit evidence of fissuring, hematoma, and thrombus formation (type VI lesions). Some type V lesions are largely calcified (type Vb), and some consist mainly of fibrous connective tissue and little or no accumulated lipid or calcium (type Vc).

As early as 1973, it was demonstrated that smooth muscle cell proliferation—thickening of the neointima—is one of the key events in atherosclerosis and that it begins as a result of endothelial cell injury that alters the structure and function of the endothelium (Ross & Glomset, Science 1973, 180, 1332-1339). In 1974 platelet-derived growth factor (PDGF) was identified as stimulating the abnormal growth and migration of smooth muscle cells into the intima of arterial lesions (Ross et al, Proc Natl Acad Sci USA. 1974, 71, 1207-1210). It was subsequently found that PDGF was synthesised by cells other than platelets involved in wound repair (macrophages, fibroblasts). In 1991, it was demonstrated that antibodies to PDGF attenuated the process of smooth muscle cell accumulation after interventional injury to the arteries of experimental animals, thereby reducing the severity of the "restenosis" lesion, which otherwise occurs (Ferns et al, Science. 1991, 253, 1129-1132).

Two complementary theories arising from the response to injury theory are currently central to thinking in the field of atherosclerotic research; namely the inflammatory mechanism (Raines, Cytokine Growth Factor Rev 2004, 15, 237-254; Levitzki, Cytokine Growth Factor Rev 2004, 15, 229-235) and the immunological mechanism (Paoletti et al, Circulation. 2004, 109 (23 Suppl 1):III20-6; Ludewig et al, J Leukoc Biol. 2004, 76, 300-306; Wick et al, Annu Rev Immunol. 2004, 22, 361-403). A large body of evidence now indicates that inflammatory processes within the vascular wall contribute to lesion formation. In a longitudinal angiographic study of the progression of atherosclerosis, evidence of disease proceeded stepwise, whereby incomplete healing followed episodes of vascular alteration (Bruschke et al, Am Heart J. 1989, 117, 296-305. In another study, infection was shown to be probably associated with intimal thickening in childhood (Willerson & Ridker, Circulation, 2004, 109, II2-110).

At each stage of atherothrombosis, inflammation has been shown to play a role (Pesonen et al, Atherosclerosis. 1999, 142, 425-429). Following injury by ox-LDL or other agents, monocytes bind at the site of the developing lesion. The adherent monocytes move into the vessel wall where they continue to ingest modified lipids and lipoproteins as they differentiate into macrophages and eventually become foam cells—macrophage cells constitute more than half of all the cells that may be released from rupture of a mature plaque. T cells and mast cells also accumulate within the lesion. Vessel wall SMCs begin to migrate and synthesise collagen while producing factors that recruit additional monocytes. Activation of the macrophages, T-lymphocytes and SMCs leads to the release of cytokines, chemokines and growth factors. In particular IL-6 is synthesized stimulating an increase in blood levels of fibrinogen, PAI-1 and C-reactive protein, as well as tissue factor (Paoletti et al, Circulation. 2004, 109(23 Suppl 1): III 20-6). Other inflammatory cytokines such as IL-1 and TNF induce the expression of cellular adhesion molecules stimulating further adhesion of leukocytes to the endothelium. Metalloproteinases synthesised by resident macrophages digest the fibrous cap of the plaque enhancing the risk of rupture and these enzymes may also be responsible for the cleavage of the adhesion molecules from damaged endothelium—soluble forms of which are increased in the blood of atherosclerotic patients (E-selectin, VCAM and ICAM) (Roldan et al, Thromb Haemost. 2003, 90, 1007-1020). Reduced NO production by the damaged endothelium leads to further platelet adherences and aggregation. The final phase of the inflammatory process occurs when the plaque ruptures releasing a large mass of prothrombotic material into blood with resulting thrombosis.

Current opinion is that the state of chronic inflammation occurring in atherosclerosis is most likely maintained by repeated and/or chronic infections (Epstein et al, Arterioscler Thromb Vasc Biol. 2000, 20, 1417-1420). A recent prospective study showed a direct relationship between the infective burden, extent of atherosclerosis and clinical prognosis (Ferns et al, Science. 1991, 253, 1129-1132), a view also reached by other studies (Espinola-Klein et al, Circulation. 2002, 105, 15-21; Georges et al, Am J Cardiol. 2003, 92, 515-521; Huittinen et al, Circulation. 2003, 107, 2566-2570). Seroreactivity against a number of bacterial and viral organisms was associated with advanced atherosclerosis. Chronic infection was significantly associated with increased death (Zhu et al, Circulation. 2001, 103, 45-51).

*Chlamydia pneumoniae* is a common respiratory pathogen. It is capable of infecting the principal cell types found in lesions and has been found atheromatous tissue obtained from endarterectomy and restenotic bypass (Gaydos et al, Infect Immun. 1996, 64, 1614-1620; Chiu et al, Circulation. 1997, 96, 2144-2148; Maass et al, J Am Coll Cardiol. 1998, 31, 827-832). The linkage of it to infection was first observed by Saiku et al who measured *C. pneumoniae*-serospecific IgG in patients with acute or chronic coronary artery disease (Saikku et al, Lancet. 1988, 2, 983-986). Although recent seroepidemiological studies show a weak correlation between positive serum antibody and cardiovascular disease (Danesh, Eur Heart J. 2002, 23, 371-375) there is more convincing correlation in histopathological studies (Bartels et al, Circulation. 2000, 101, 137-141).

*Helicobacter pylori*, a resident of human gastric epithelium, is implicated by several serological studies, which indicate a significant association with atherosclerotic disease (Espinola-Klein et al, Circulation. 2002, 105, 15-21; Georges et al, Am J. Cardiol. 2003, 92, 515-521; Huittinen et al, Circulation. 2003, 107, 2566-2570).

Human cytomegalovirus (HMCV) is a member of the herpesvirus family, several members of which show a strong association with the cardiovascular system. Several seroepidemiological studies have shown a link to atherosclerosis (Zhou et al, N Engl J. Med. 1996, 335, 624-630; Adam et al Lancet. 1987, 2, 291-293). Moreover there is direct evidence of the virus in arteries from patients (Hendrix et al, Am J Pathol. 1989, 134, 1151-1157). HMCV can infect all types of cell types in the vascular wall, stimulating the synthesis of chemokines and cytokines (Jarvis & Nelson, Opin Microbiol. 2002, 5, 403-407).

Members of the family of Toll-like receptors (one of which forms a signal transducing complex with the LPS receptor CD14) are pathogen pattern recognition receptors that are thought to mediate the inflammatory response following infection (Kiechl et al, Ann Med. 2003, 35, 164-171; Arroyo-Espliguero et al, Heart. 2004, 90, 983-988; Pasterkamp et al, Eur J Clin Invest. 2004, 34, 328-334) through activation of the NF-kappa B pathway, which initiates synthesis of cytokines and chemokines (Muroi et al, J Biol Chem. 2002, 277, 42372-42379). Interestingly certain polymorphisms of Toll receptors are associated with enhanced risk of disease (Kiechl et al, N Engl J Med. 2002, 347, 185-192; Ameziane et al, Arterioscler Thromb Vasc Biol. 2003, 23, 61-64).

The concept of molecular mimicry provides an elegant framework as to how cross-reactivity between antigens from a foreign agent with self-proteins may trigger autoimmune diseases. Either the molecules or their conformational fits may be shared, even though their origins can be separated as an evolutionary side as, for example, a virus and a human. An immune response against an epitope shared by the host and virus can evoke a tissue-specific immune response that is thought to be capable of eliciting cell and tissue destruction. This is brought about generating cytotoxic cross-reactive effector lymphocytes or antibodies that recognise specific determinants on target cells. By a complementary mechanism, the microbe can induce cellular injury and release self-antigens, which generate immune responses that cross-react with additional but genetically distinct self-antigens.

Infection of cells in the vascular wall may initiate a cascade of inflammatory reactions and may lead to the destruction of cells via direct cytopathicity. It has been reported that atherosclerosis in hypercholesterolaemic low-density lipoprotein receptor (LDLR) mice is significantly reduced in the absence of monocyte chemoattactant protein-1 (MCP-1) (Gu et al, Mol. Cell 1998, 2, 275-281) or the combined absence of P- and E-selectins (Dong, et al, J. Clin. Invest. 1998, 102, 145-152). Pathogen-specific immune responses are induced when the infectious agent or its antigens reach secondary lymphoid organs (Karrer et al, J. Exp. Med. 1997, 185, 2157-2170). Cross-reactive Th cells recognising microbial and self-antigens may be generated during viral and bacterial infections (Oldstone, Cell 1987, 50, 819-820). The peripheral activation of pathogen-induced Th cells, recognising self-antigens presented by tissue-resident APC, may result in the release of cytokines such as IFN-γ and chemokines, which attract further T cells and macrophages to the vascular lesion. Release of self-antigens from endothelial or smooth muscle cells and their subsequent uptake and transport to secondary lymphoid organs elicit genuine autoimmune responses. Epitope spreading may lead to perpetuation of the inflammatory response by formation of antigen-antibody complexes and local activation of self-reactive Th cells.

Macrophages activated by immune complexes and/or Th cell-derived soluble factors may secrete oxidative intermediates, cytokines, or metallo-matrix proteases (MMPs) (FIG. 2c). Chemokines and cytokines secreted by pathogen-specific Th cells attract and may stimulate self reactive "bystander" Th cells in a T cell receptor-independent manner. IFN-α, producing autoimmune Th cells and activated macrophages, contributes to the perpetuation of the local inflammatory response.

Molecular mimicry may play an important role in atherogenesis, as structurally related human and chlamydial heat shock proteins (HSP60/65) can be found in atherosclerotic lesions (Kol et al, Circulation 1998, 98, 300-307). It has been shown, for example, that immunisation of mice with recombinant bacterial HSP65 enhanced early lesion in mice fed a high cholesterol diet (George et al, Arterioscler. Thromb. Vasc. Biol. 1999, 19, 505-510) and that HSP65-specific T cells or antibodies can promote fatty-streak formation in LDLR-deficient mice (George et al, J. Am. Coll. Cardiol. 2001, 38, 900-905). Cross-reactive T cells (Kiechl et al, N Engl J Med. 2002, 347, 185-192) and the direct macrophage-stimulatory function of HSP60 (Xu et al, J. Clin. Invest. 1993, 91, 2693-2702) may lead to the secretion of cytokine, MMPs and NO by macrophages, thereby fueling inflammatory reactions in the induced major histocompatiblity complex class II expression on endothelial cells by suppressing Th cell activation (Kwak et al, Nat. Med. 2000, 6, 1399-1402). A recent prospective, double-blind, placebo-controlled trial in 40 male patients with coronary artery disease revealed that the macrolide antibiotic azithromycin has a favorable effect on endothelial function (Parchure et al, Circulation 2002, 105, 1298-1303). Likewise, antibiotic treatment can significantly reduce adverse cardiac events in patients presenting with acute coronary syndromes (Stone et al, Circulation 2002, 106, 1219-1223) or acute non-Q-wave coronary syndrome (Sinisalo et al, Circulation 2002, 105, 1555-1560).

Several *C. pneumoniae* antigens have been identified that induce protective immunity in a mouse model of acute *C. pneumoniae* infection (Murdin, J. Infect. Dis. 2000, 181 (Suppl. 3), S544-S551). Furthermore, vaccination approaches using autoantigens such as oxLDL (Palinski et al, Proc. Natl. Acad. Sci. USA 1995, 92, 821-825; Zhou et al, Arterioscler. Thromb. Vasc. Biol. 2001, 21, 108-114) or HSP60/65 (Maron et al, Circulation 2002, 106, 1708-1715) in experimental animals showed some beneficial effects. The great challenge for the future is thus to translate the results from the encouraging experimental stage into clinical studies.

It has been suggested that cross-reactivity between antigens from a foreign agent with self-proteins may trigger autoimmune diseases. An immune response against a shared epitope can evoke a tissue-specific immune response that is thought to be capable of eliciting cell and tissue destruction. This is brought about generating cytotoxic cross-reactive effector lymphocytes or antibodies that recognise specific determinants on target cells. By a complementary mechanism, the microbe can induce cellular injury and release self-antigens, which generate immune responses that cross-react with additional but genetically distinct self-antigens.

Infection of cells in the vascular wall may initiate a cascade of inflammatory reactions and may lead to the destruction of cells via direct cytopathicity. Atherosclerosis in hypercholesterolaemic low-density lipoprotein receptor (LDLR) mice is significantly reduced in the absence of monocyte chemoattactant protein-1 (MCP-1) (Gu et al, Mol. Cell 1998, 2, 275-281) or the combined absence of P- and E-selectins (Dong, et al, J. Clin. Invest. 1998, 102, 145-152). Pathogen-specific immune responses are induced when the infectious agent or its antigens reach secondary lymphoid organs (Karrer et al, J. Exp. Med. 1997, 185, 2157-2170). Cross-reactive Th cells recognising microbial and self-antigens may be generated during viral and bacterial infections (Oldstone, Cell 1987, 50, 819-820). The peripheral activation of pathogen-induced Th cells, recognising self-antigens presented by tissue-resident APC, may result in the release of cytokines such as IFN-γ and chemokines, which attract further T cells and macrophages to the vascular lesion. Several *C. pneumoniae* antigens have been identified that induce protective immunity in a mouse model of acute *C. pneumoniae* infection (Murdin, J. Infect. Dis. 2000, 181 (Suppl. 3), S544-S551).

Furthermore, vaccination approaches using autoantigens such as oxLDL (Palinski et al, Proc. Natl. Acad. Sci. USA 1995, 92, 821-825; Zhou et al, Arterioscler. Thromb. Vasc. Biol. 2001, 21, 108-114) or HSP60/65 (Maron et al, Circulation 2002, 106, 1708-1715) in experimental animals showed some beneficial effects. The great challenge for the future is thus to translate the results from the encouraging experimental stage into clinical studies.

In addition a number of other approaches to developing anti-atheroma vaccines based on autoantigens, particularly those related to lipid metabolism, have previously been investigated. T cells extracted from human atherosclerotic plaques have been shown to recognise oxidised low density lipoprotein (oxLDL) and immunisation of LDL-deficient rabbits with molondialdehyde-modified LDL was shown to reduce atherosclerosis (Palinski et al, Proc. Natl. Acad. Sci. USA 1995, 92, 821-825). International application WO 01/68119 discloses antigenic compositions based on such modified LDL or apoB100 immunogens. Another target for such approaches is cholesterol ester transferase protein (CETP) modulation of the activity of which may be beneficial in preventing the progression of atherogenesis. International application WO 97/41227 discloses a DNA vaccine approach using a plasmid encoding various T and B-cell CETP epitopes. Attempts have also been made to target cholesterol directly (WO 92/10203).

Bispecific antibodies are antibodies designed to bind different immunogens on each of their binding arms. The term 'bispecific' as used herein refers to antibodies with two specific antigen-binding sites capable of binding to two distinct epitopes. Such antibodies are sometimes referred to as 'bifunctional', but this is ambiguous since it strictly implies two separate functions and naturally occurring monospecific antibodies can be said to have both antigen binding/neutralising functions and Fc-dependent effector functions (Hudson & Souriau, Nature Medicine 2003, 9:129-134). Bifunctional antibodies can be used to bind to two separate immunogens simultaneously, binding to one immunogen while "carrying" another immunogen along, etc. Bispecific monoclonal antibodies produced by conventional chemical methods have proved useful in the immunodiagnosis and immunotherapy of cancer, atherosclerosis and other diseases. Recombinant antibodies produced by genetic engineering techniques have also become available for use in preclinical and clinical studies. Furthermore, through genetic engineering, it is possible to remove or add on key protein domains in order to create designer antibody molecules with two or more desired functions.

Conventionally prepared bispecific and bifunctional monoclonal antibodies have already shown promise in clinical trials and results from preclinical studies of recombinant bispecific antibodies are encouraging. Technology for humanising or CDR drafting monoclonal antibodies to minimise the host immune response against the antibody itself are well-known in the art (Hudson & Souriau, Nature Medicine 2003, 9:129-134). Synthetic phage libraries have been created which use randomised combinations of synthetic human antibody V-regions. By selection on antigen so called 'fully human antibodies' can be made in which it is assumed the V-regions are as human as in nature. Transgenic mice have been created which have a repertoire of human immunoglobulin germline gene segments. These mice when immunised thus make human-like antibodies.

For a number of reasons, the use of recombinant human monoclonal antibodies is becoming increasingly popular due to their advantages compared to conventional monoclonal or polyclonal antibodies. For instance, the production of recombinant antibodies avoids using animals. Also the production of recombinant antibodies is much faster compared to conventional antibody production and they can be generated against an enormous number of antigens. In contrast, in the conventional method, many antigens prove to be non-immunogenic or extremely toxic, and therefore can't be used to generate antibodies in animals. Moreover, affinity maturation (i.e. increasing the affinity and specificity) of recombinant antibodies is very simple and relatively fast. Finally, large numbers of different antibodies against a specific antigen can be generated in one selection procedure. Libraries of antibodies with different antigen recognition sites can be made in several ways: (a) generation of a synthetic repertoire by cloning synthetic CDR3 regions in a pool of heavy chain germline genes. This is capable of generating a large antibody repertoire, from which recombinant antibody fragments with various specificities can be selected (Nissim et al, EMBO J. 1994, 13, 692-698). (b)

Searching the latest (and largest; $10^{12}$ epitopes) synthetic antibody libraries. (c) Using the lymphocyte pool of humans as starting material for the construction of an antibody library. It is possible to construct naive repertoires of human IgM antibodies and thus create a human library of large diversity (Marks et al, J. Mol. Biol. 1991, 222, 581-597) (d) Another possibility is to prepare so-called patient libraries. First, the sera of individuals (for example, autoimmune patients) are tested for the presence of specific antibodies directed to the antigen of interest. From the lymphocyte pool of positive individuals, IgG libraries can be generated, which will contain antibodies of high specificity and with high affinity. Construction of such specialised libraries will enable us to generate antibodies for studying specific biomolecules e.g. libraries from patients with atherosclerosis for selection of markers, or libraries adapted for the generation of antibodies against specific molecules such as sugar residues.

Once libraries are generated, they can be used for the selection of recombinant antibodies against various antigens, by immobilising the antigen of interest and applying various selection rounds with the appropriate phage display libraries.

In order to obtain the most selective antigen epitopes, phage display screening method can be employed in which target protein is added to a library of M13 phages in which each individual phage displays a random-sequence peptide insert in either protein g3p or g8p. Thousands peptides with 6-15 amino acid residues can be chosen between libraries, eg. starting out with a 9-mer library with the random peptides inserted in the core protein g8p. Such libraries offer the advantage of multimeric binding (several hundred copies of the peptide are displayed on each phage), and the peptide sequences identified from the binding phages often reveal sequence themes that make it easier to narrow in on the consensus sequences that bind to target proteins. Depending on the nature of the target protein, a variety of techniques can be used for isolation of phages displaying relevant peptide binders. After identification of phages that bind the target protein, they will be subcloned and amplified prior to DNA-sequencing. A listing of the DNA-sequences and of the corresponding peptide inserts will be obtained. A standard approach is to immobilise the target protein on magnetic beads followed by adsorption of phages that bind to the target protein. After careful washing of the beads, the bound phages are eluted and amplified in $E.\ coli$. The procedure may be repeated a couple of times to enrich the binding phages. The binding phages are then amplified on a lawn of $E.\ coli$, and the resulting plaques are blotted onto nitrocellulose membranes. The membranes are incubated with a dilution of your target protein, and the binding is verified using a suitable detection system such as an enzyme-labelled antibody or using enzyme labeled streptavidin on biotinylated targets.

DNA vaccination differs from traditional vaccines in that only the DNA coding for a specific peptide epitope is injected (Locher et al, Curr Opin Mol Ther 2004, 6, 34-39; Boyd et al, 2003, 6, 1155-1164; Karin, Curr Opin Mol Ther 2004, 6, 27-33). The DNA can be administered either in a saline solution injected through a hypodermic needle or on DNA-coated gold beads propelled into the body using gene guns. The actual production of the immunising protein takes place in the vaccinated host. DNA vaccination provides long-lived immune responses, unlike conventional vaccines that require multiple inoculations to maintain immunity. It is also possible to give vaccines against multiple antigens in a single inoculation. The ability to use generic production methods greatly simplifies vaccine development and the production process. DNA vaccines are extremely stable and can be stored under a vast array of conditions eliminating the need for refrigerators to maintain a vaccine during distribution.

Platelet Derived Growth Factor: Structure and Function.

Platelet derived growth factor (PDGF) includes a family of homo- and heterodimeric proteins consisting of disulphide bonded A- and B-polypeptide chains (Waterfield et al, Nature 1983, 304, 35-39; Uutela et al, Circulation 2001, 103, 2242-2247). Although some cell types exhibit coordinate expression of the PDGF genes, in general, the expression of each is independent (Heldin et al, Physiol Rev 1999, 79, 1283-1316). Since a wide range of extracellular stimuli effect the expression of each, it is thought that the level of synthesis may be cell-specific.

Structurally, PDGF is one of the cysteine knot family of cytokines, which includes VEGF (Sun & Davies, Annu Rev Biophys Biomol Struct 1995, 24, 269-291). Two cysteine residues form the link between the two subunits while the other six residues are engaged in intra-chain disulphide bonds. The crystal structure of PDGF showed that the two subunits are arranged in an anti-parallel manner forming a tight knot like structure. Two large loops (1 and 3) stabilised by β-sheet interactions extend in one direction from this knot and another shorter loop 2 extends in the opposite direction) (Oefner et al, EMBO J 1992, 11, 3921-3926). In the dimer, loops 1 and 3 of one subunit are close to loop 2 of the other PDGF isoforms exert their effects upon target cells by activating two structurally related protein tyrosine kinases. The α and β-receptors have molecular masses of around 180 kDa and consist of five immunoglobulin-like domains linked to the intracellular tyrosine kinase domain (Heldin & Westermark, Rev 1999, 79, 1283-1316). The epitopes responsible for binding to the receptors have been investigated using site-directed mutagenesis and the amino acid residues that are the most important for binding have been localised in loops 1 and 3 (to a lesser degree, loop 2 is also involved) (Clements et al, EMBO J 1991, 10, 4113-4120; Andersson et al, Growth Factors 1995, 12, 159-164; Fenstermaker et al. J Biol Chem 1993, 268, 10482-10489).

Of the three isoforms only PDGF-BB interacts with both receptors with equal affinity. The activation of the cell by PDGF occurs following dimerisation of two receptors by the binding to a single dimeric PDGF molecule. The phenotypic changes that are caused by activation of each of the PDGF α and β receptor homodimers show some differences (Heldin et al, Physiol Rev 1999, 79, 1283-1316).

The Physiological Function of PDGF.

PDGF has fundamental functions in embryogenesis (perinatal death occurs in knock out mice). In a PDGF-B chain knockout mouse model, for example, defective kidney and blood vessels were found as well as heart defects (Leveen et al, Genes Dev 1994, 8, 1875-1887). Connective tissue producing cell types are particularly dependent upon PDGF. The significant role of PDGF in the formation of connective tissue is also important during wound healing in the adult (Werner & Grose, Physiol Rev 2003, 83, 835-870).

PDGF in Atherosclerosis.

Although there are continuing reports of the involvement of PDGF in tumour growth and fibrotic disease, atherosclerosis has been the principal focus of research interest.

PDGF occurs at only low levels in the arteries of healthy adults but its expression is increased in situations in which there are inflammatory-fibroproliferative mediated changes to blood vessels. Thus in naturally occurring atherosclerosis (Wilcox et al, J Clin Invest 1988, 82, 1134-1143; Rubin et al, Lancet 1988, 1, 1353-1356; Ross et al, Science 1990, 248, 1009-1012; Libby et al, N Engl J Med 1988, 318, 1493-1498; Uchida et al, Atherosclerosis 1996, 124, 9-23) in experimental models of atherosclerosis (Ross et al, Science 1990, 248, 1009-1012; Golden M A, Au Y P, Kirkman T R, et al. J Clin Invest 1991, 87, 406-414) as well as in the coronary arteries of patients following PTCA (Kanzaki et al, Eur J Clin Invest 1994, 24, 377-381; Ueda et al, Am J Pathol 1996, 149, 831-843; Ueda et al, Heart 1996, 75, 549-556; Misiakos et al. Eur Surg Res 2001, 33, 264-269.) increased expression of PDGF and PDGF receptors have been reported. It appears that the elevated levels of PDGF in the vessel wall arise from the released products of platelet thrombi as well as from protein synthesised by macrophages, SMC or endothelial cells (Bohm et al, Zentralbl Pathol 1994, 140, 357-362). Once there, PDGF is thought to stimulate SMC migration from the media of the vessel to the intima layer as well as synthesis of matrix molecules.

A number of studies have demonstrated a direct involvement of PDGF in intimal thickening. Intimal hyperplasia following balloon catheterisation of rat arteries may be blocked by the infusion of neutralising PDGF antibodies (Ferns et al, Science 1991, 253, 1129-1132). The development of aortic lesions in cholesterol fed rabbits is inhibited by prior immunisation with PDGF-BB (Rutherford et al, Int J Exp Pathol 1997, 78, 21-32). In addition a low molecular weight PDGF receptor kinase inhibitor has been shown to inhibit neointimal formation. Moreover the administration of additional PDGF BB enhances intimal thickening in animal models (Jawien et al, J Clin Invest 1992, 89, 507-511). Neutralising antibodies to the receptor have also been shown to inhibit intimal thickening in baboon and rat models. In addition, antisense oligonucleotides to the receptor have been shown to reduce thickening (Lin et al, J Vasc Res 2004, 41, 305-313; Deguchi et al. Gene Ther 1999, 6, 956-965; Sirois et al, Circulation 1997, 95, 669-676). Such observations have suggested that blockade of the PDGF pathway may be useful in controlling restenosis following angioplasty. Clinical trials using low molecular weight blockers of PDGF are giving encouraging results (Lassila et al. Thromb Vasc Biol 2004, 24, 935-942; Levitzki, Growth Factor Rev 2004, 15, 229-235; Sihvola et al. Transplantation 2003, 75, 334-339; Bilder et al. Circulation 1999, 99, 3292-3299; Fishbein et al, Arterioscler Thromb Vasc Biol 2000, 20, 667-676; Yamasaki et al, Circ Res 2001, 88, 630-636).

HSP65: Current Understanding of Structure and Function

General Background of HSPs:

Heat-shock proteins are a group of proteins that assist in the assembly, folding, and translocation of other proteins. In addition, they protect the cell against heat injury or other forms of stress. All cells, prokaryotic and eukaryotic, are able to respond to different cellular stresses by synthesizing these proteins. Heat shock proteins are highly conserved, ubiquitously distributed, and involved in important aspects of viral and bacterial infections, autoimmune diseases, and in cancer immunity.

HSPs are multigene families that range in molecular size from 10 to 150 kDa and are found in all major cellular compartments. According to molecular weight, they are divided into following families: HSP10, small HSPs, HSP40, HSP60, HSP70, HSP90, and HSP110. HSPs widely distributed in virtually all organisms, including Chlamydiae and humans.

Structure of HSPs:

HSP65 is homologous to HSP60 and can be classified as a member of HSP60 family which are molecular chaperones including members HSP58, HSP65 and Grp58 (glucose-related protein58). Hsp60-chaperonin family Includes GroEL (*Escherichia coli* HSP) from bacteria, rubisco-binding protein from chloroplasts, HSP60 from mitochondria, and the t-complex polypeptide 1 from eukaryotic cystosol. *Escherichia coli* GroEL and GroES are the prototypical chaperonin and co-chaperonin.

The most studied HSP60-like protein is the GroEL found in *Escherichia coli*. This particular chaperonin's structure has been solved by X-ray crystallography to resolution of 2.8 A. The structure consists of a porous cylinder of 14 subunits made of two nearly 7-fold rotationally symmetrical rings stacked back-to-back with dyad symmetry. Each subunit consists of three domains: a large equatorial domain that forms the foundation of the assembly at its waist and holds the rings together; a large loosely structured apical domain that forms the ends of the cylinder; and a small slender intermediate domain that connects the two (Braig & Otwinowski, Nature, 1994, 371, 578-584). GroEL is also slightly taller than it is wide with a central cavity or channel that may be used to link polypeptides. The large central cavity appears to traverse the entire length of the cylinder with no obstruction. This contrasts with electron microscopy reconstructions which show density completely obstructing the channel at both the apical and equatorial levels of each ring. Given conclusions about the function of the apical domain in peptide binding, the electron microscopy densities near the channel opening could be derived from bound polypeptides on the inside portions of the hollow cylinder. Hsp60 proteins are composed of 14 subunits arranged in two stacked 7-membered rings. An unfolded protein binds to large hydrophobic surfaces inside the central cavity. ATP binding triggers rotation of the Hsp60 subunits such that the hydrophobic surface turns toward the neighboring Hsp60 subunit.

HSP60 Functions:

Carotid atherosclerosis has been reported to associate with serum soluble HSP60, whose role in activating proinflammatory processes has been related to early vessel pathology (Nagiano M, et al., Immunol. 2005; 174: 6509-6517; Xiao Q, et al., Stroke 2005; 36: 2571-2576). High levels of autoantibodies against 60-kDa members of the hsp60 family were associated with atherosclerosclerotic vascular diseases (Xu Q, et al., Lancet. 1993; 341: 255-259; Xu Q, et al. Circulation. 1999; 100: 1169-1174; Birnie D H, et al. Lancet. 1994; 344: 1443; Hoppichler F, et al. Atherosclerosis. 1996; 126: 333-338). Bason et al have identified an 11 amino acid sequence of HSP60 that is recognized by most patients with coronary-artery disease (Bason C, et al., Lancet. 2003; 362:1971-7).

HSP65 Functions:

The Hsps work in series to unfold and then again to refold proteins as they pass across membranes, such as those in the nucleus and mitochondria. During bacterial infection, host cells are activated by bacterial chaperonin 60 proteins that are secreted or expressed on the outer surface of bacteria. Hsp60 has been shown to have several immunological effects, including the induction of pro-inflammatory cytokine secretion from, and adhesion molecule expression on, a number of myeloid and vascular cell types, including smooth muscle cells. This induces host cells to produce cytokines or other intercellular signals. It may also cause them to release their own chaperonins, which in turn activate other host cells. Bacterial or host chaperonins are identified by the host via presentation of a part of the chaperonin on the major histocompatibility complex (MHC). This activates T cells via the T-cell receptor (TCR). Additionally, B cells are activated by chaperonins to produce antibodies. Errors in this response may lead to some forms of autoimmune disease, owing to the recognition of self-chaperonin molecules. HSP65 has been reported as having a role in carotid athrosclerosis (Lassila et al, Arterioscler Thromb Vasc Biol 2004, 24, 935-942), coronary heart disease (Hoppichler et al, Atherosclerosis 1996, 126, 333-338) and borderline hypertention (Frostegard et al, 1997, 29, 40-44). Patents with blood containing high levels of antibodies to HSP65 were found to be at increase risk of subsequent cardiovascular events (Veres et al, Circulation 2002, 106, 2775-2780). HSP65 also has been proposed as a target antigen in type 1 diabetes (Elias et al, Proc Natl Acad Sci USA. 1990, 87, 1576-1580), and arthritis (Durai et al, J Immunol, 2004, 173, 181-188). It has been demonstrated that elevated levels of anti-mycobacterial HSP65 antibodies, cross-reacting with human HSP60, serve as a prognostic marker for the incidence, prevalence, severity, and progression of carotid athrosclerosis in a clinical health population. Antibodies to microbial HSP60/65 recognise specific epitopes on human HSP60. These cross-reactive epitopes were shown to serve as immune targets in incipient atherosclerosis and might provide further insights into the mechanisms of early atherosclerosis (Perschinka et al, Arterioscler Thromb Vasc Biol. 2003, 23, 1060-1065).

Other Targets
Oxidised LDL (OxLDL):

OxLDL was originally thought to be involved in atherosclerotic signaling because it accounts for the loading of macrophages with cholesterol, but it quickly became apparent that oxLDL had many other properties that were potentially pro-atherogenic. Interest has been based in part on in vitro studies that demonstrated (a) that minimally oxLDL stimulates endothelial expression of macrophage chemoattractants (Cushing et al, Proc Natl Acad Sci USA. 1990, 87, 5134-518), adhesion molecules (Berliner et al, J Clin Invest. 1990, 85, 1260-1266) and cytokines (Rajavashisth et al, Nature. 1990, 344, 254-257) and (b) that extensively oxLDL is taken up by macrophage scavenger receptors in a manner that is unregulated by cell cholesterol content (Henriksen et al, Proc Natl Acad Sci USA. 1981, 78, 6499-6503; Witztum J L. Role of oxidised low density lipoprotein in atherogenesis. Br Heart J. 1993, 69, S12-S8).

Extensively oxLDL has a number of other potentially proatherogenic effects, including cytotoxicity and its induction of expression of plasminogen activator inhibitor-1 by endothelial cells, of platelet-derived growth factor A-chain by smooth muscle cells (SMCs), of interleukin-1β, interleukin-8, and stress proteins by macrophages; and activation of T lymphocytes. Toshima et al. recently, using an alternative monoclonal antibody, showed that oxLDL was higher in subjects with established coronary heart disease as compared to controls (Toshima et al, Arterioscler Thromb Vasc Biol. 2000, 20, 2243-2247; Suzuki et al, Clin Biochem. 2002, 35, 347-353). OxLDL, therefore, can be an antigen presented in atherosclerosis lesions. Several macrophage membrane proteins have been shown to bind oxLDL including human monocyte antigen CD36, a closely related scavenger receptor, SR-BI, a 94-97 kDa protein homologous to CD68 (Ramprasad et al, Proc Natl Acad Sci USA. 1995, 92, 9580-9584).

Early human atherosclerotic lesions of fetuses and children contain modified lipoproteins, in particular, oxidized low-density lipoproteins (oxLDL) (Napoli C, Palinski W. Eur. Heart J. 2001; 22: 4-9). Substantial evidence suggests that oxLDL and oxidized phosphatidylcholines (PtC, PC-containing phospholipids), prominent components of oxLDL, have many proinflammatory and proatherogenic properties (Napoli C, et al., J. Clin. Invest. 1997; 100:2680-90; Nishi K, et al., Arterioscler Thromb Vasc Biol. 2002; 22: 1649-1654.). Recent reports have demonstrated that several aldehyde-modified peptide sequences taken from apolipoprotein B-100 (apoB-100) can be major targets for immune responses (Hulthe J. Clin Chim Acta. 2004; 348:1-8).

β2-Glycoprotein I (β2-GP I), a phospholipid binding protein, bears the most common epitope for antiphospholipid antibodies and is cleaved with lipoprotein. This protein is also referred to as apolipoprotein H (Apo H). Human β2-GP I is a single-chain molecule consisting of 326 amino acid residues and 5 carbohydrate chains and has a molecule mass of approximately 55 kDa. The protein contains 5 internal repeat units of 60 amino acid residues, each with 2 internal disulphide bonds, known as Sushi domain 118 (Bouma et al, EMBO J. 1999, 18, 5166-5174; Schwarzenbacher et al, EMBO J. 1999, 18, 6228-6239). Antiphospholipid (aPL) antibodies show cross-reactivity against oxidized LDL (Witztum & Horkko, Ann. NY Acad. Sci. 1997, 811, 88-96; Horkko et al, J. Clin. Invest. 1996, 98, 815-825) and may thereby be associated with an increased risk of atherosclerosis (Vaarala, Lupus, 1996, 5, 442-447).

Oxidised Phosphatidylcholine.

OxLDL contains a variety of oxidation neoepitopes on both the protein and lipid moieties. Of particular interest in generating such epitopes are reactive decomposition products of phosphatidylcholine (PC), such as 1-palmitoyl-2-(5-oxovaleroyl)-sn-glycero-3-phosphorylcholine (POVPC) which are capable of modifying LDL protein and lipid to form covalent adducts. Modification by agents such as POVPC and malonodialdehye are thought to lead to the formation of the neo-self epitopes. These modifications along with the phosphorylcholine-containing oxidised phospholipids themselves are thought to contribute to interaction of LDL with scavenger and Toll receptors.

Cytomegalovirus:

Human cytomegalovirus (HCMV) is a species-specific betaherpesvirus that infects a majority of the population worldwide (Stern, J. IL. et al., The Journal of Immunology, 2008; 180: 6577-6585). CMV infection also promotes the development of chronic allograft vasculopathy (characterized by graft vessel arteriosclerosis) that underlies late graft failure (Grattan M T, et al., JAMA 1989; 261: 3561-3566; Everett J P, et al., J. Heart Lung Transplant. 1992; 11: S133-S137). The activation of TGF-β1 by integrin αvβ6 contributes to pathological changes and may impair endothelial cell functions in tissues that are chronically infected with CMV (Tabata T, et al., American Journal of Pathology. 2008; 172:1127-1140). It has been demonstrated that infections with a single high dose of mouse CMV (MCMV) aggravate the atherosclerotic lesion progression in apoE−/− mice following an initial rise in circulating interferon-γ(IFN-γ) and tumor necrosis factor-α levels (Hsich E, et al., Atherosclerosis 2001; 156: 23-8; Burnett M S, et al., J Infect Dis 2001; 183: 226-31). Animal models have confirmed that infection with CMV is capable of accelerating arteriosclerosis (Stassen F R, et al., J Clin Virol 2006; 35:349-353).

*Chlamydia pneumoniae* (Cpn):

The first evidence linking Cpn infection and atherosclerosis was obtained from the finding that individuals with coronary heart disease and acute myocardial infarction were found to have significantly higher titres of Cpn-specific IgG antibodies than that in individuals without cardiovascular disease (Saikku P, et al., Lancet. 1988; 2: 983-986). Subsequent studies found that Cpn infection is resident among arterial fatty streaks, as well as in advanced atherosclerotic plaques (Shor A, et al., S Afr Med. J. 1992; 82: 158-161; Kuo C C, et al., J Infect Dis. 1993; 167: 841-849). It was estimated that Cpn is present in approximately 50% to 60% of atheromatous tissue, whereas the prevalence in samples from patients without evidence of atherosclerosis is less than 5% (Shor A, Phillips J I. JAMA. 1999; 282: 2071-2073). It is also possible to isolated and culture the bacterium from atherosclerotic lesions (Ramirez J A. Ann Intern Med. 1996; 125: 979-982), indicating that the pathogen is not only viable but is also capable of active replication. Thus, the present body of evidence is highly suggestive of a causal role for Cpn infection in atherosclerosis. Case-control studies revealed that specific anti Cpn antibody levels were significantly higher in patients with CVD than in control patients and a follow-up study indicated that high antibody titres to Cpn were associated with an increased risk of clinical event (Virok D, et al., Stroke 2001; 32:1973-6).

*Porphyromonas gingivalis* (*p. gingivalis*):

Significant associations between atherosclerosis and both *Porphyromonas gingivalis*, a major periodontopathogen, have been shown (Ford et al., J Dent Res. 2007; 86: 35-40). *Porphyromonas gingivalis* has been shown to accelerate atherosclerotic lesion development in hyperlipidemic animals (Koizumi et al., Infect Immun. 2008; 76: 2958-65).

The Use of Cell Specific Peptide/HSP Complexes in the Development of Immunotherapy HSPs have an inherent ability to bind non-covalently to the large array of peptides generated within cells during protein synthesis as well as during intracellular degradation and removal of protein. Some of these peptide/HSP complexes will be phenotype specific and can be used for the generation of immune response against abnormal cells (Xu, Thromb Vasc Biol 2002, 22, 1547-1559). In fact, the immunological function of HSPs was first discovered when it was observed that certain HSPs (hsp70, hsp90 and gp96), when purified from tumours, could elicit an immunological reaction against that specific tumour (Blachere et al, J Immunother 1993, 14, 352-356; Nieland et al, Proc Natl Acad Sci USA 1996, 93, 6135-6139). Subsequent studies indicated that the immunogenicity was due to tumour specific antigenic peptides complexed to the HSP. In addition to carrying antigenic peptides for presentation, the HSP/antigen complexes stimulated the secretion of pro-inflammatory cytokines by macrophages and dendritic cells as well as maturation of dendritic cells. These immunological properties have generated great interest in the use of HSPs as immuno-adjuvants against cancer and infectious disease (Nieland et al, Proc Natl Acad Sci USA 1996, 93, 6135-6139; Pockley, Expert Rev Mol Med, 2001, 1-21; Manjili, Front Biosci 2002, 7, d43-52; Lamb, Atherosclerosis 2003, 167, 177-185; Lewis, Proc Natl Acad Sci USA, 2004, 101, 14653-14656). This is an approach that is applicable to individual tumours since HSP/antigenic peptides can be isolated from resected tumour tissue and used for immunisation (autologous immunisation)

More recently, it has become clear that heat shock proteins (in particular Hsp70, Hsp90 and calreticulin) deliver potentially antigenic peptides to antigen presenting cells by binding intracellular self peptides with extremely high affinity, and, on being released from the cell by lysis, binding to antigen presenting cells expressing the Hsp receptor CD91 (Basu et al, 2001 Immunity 14: 303-313.). The cellular stress before lysis increases the levels of heat shock proteins and so increases this effect. It has been proposed that stimulation of the immune response against intracellular antigens is related to necrotic, rather than apoptotic, or programmed, cell death and that this is, at least partly, controlled at the level of antigen presenting cells (Matzinger, 1994 Annu Rev Immunol 12: 991-1045.). As applied specifically to anti-tumour responses, it has been shown that non-apoptotic (ie necrotic) cell death of tumour cells induces higher levels of Hsp70 and is associated with increased immunogenicity, release of inflammatory cell contents, increased secretion of pro-inflammatory Th1-type cytokines and macrophage activation (Gough et al, 2001 Cancer Research 61: 7240-7247). Apoptotic cell death, on the other hand, in which intracellular macromolecules are degraded before being exposed to the extracellular environment, and Hsp70, Hsp90 and calreticulin are not released in significant amounts (Basu et al, 2000 Int Immunol. 12: 1539-1546.) in general fails to initiate inflammatory and immune responses. Necrotic, but not apoptotic, cell lysates cause maturation of dendritic cells, the key antigen presenting cells for activating naïve T cells in the initiation of an immune response (Galucci et al, 1999 Nat Med 5: 1249-1255; Sauter et al, 2000. J Exp Med 191: 423-434. Hsp70 itself has been shown to be a maturation factor for dendritic cells (Kuppner, et al, 2001 Eur J Immunol 31:1602-1609; Gastpar et al, European Patent Application EP1209226). In addition, apoptotic cells may deliver specific anti-inflammatory and immunosuppressive signals directly to antigen presenting cells, for example through the phosphatidylserine receptor (Fadok et al, 2000 Nature 405: 85-90.).

We have previously developed several bifunctional molecules using a protein scaffold such as dendroaspin (WO 01/57210). Dendroaspin is an RGD-containing venom protein, isolated from the venom of *Dendroaspis jamesonii*. Dendroaspin is a three-looped structure with a well-defined fold. The orientation of RGD-containing loop III is completely different from that in other short chain neurotoxins such as erabutoxin b, and is displaced from the other 2 loops (FIG. 1). The loop II and III have been used for the insertion of different protein domains and shown different functional features with structural modulation.

Oral Pathology and Cardiovascular Disease

Epidemiological studies on humans as well as animal models have shown evidence of association between coronary artery disease (CAD) and oral infections especially periodontitis (Matilla, BMJ 1989, 779; de Stefano, BMJ 1993, 306, Beck, J. Periodontol, 1996 1123; Scannapeco, Ann. Periodontal 2003, 38). Periodontitis is a chronic destructive inflammatory condition that encompasses the spectrum of gum inflation (gingivitis) and progressive detachment of gums (severe periodontitis) to reduce in bone alveolar density that results in tooth loss. Oral bacteria such as *Porphyromonas gingivalis, Actinobacillus actinomycetemcomitans, Tannerella forsythensis, Treponema denticola* and *Campylobacter rectus* have been implicated in the aetiopathogenesis of the disease. Thus, infection of the periodontium provides a chronic reservoir of inflammatory mediators like cytokines and lipopolysaccharides, which contribute to the atheroma formation. The role of traditional risk factors in the pathogenesis of CAD has been well established but it does not fully account for the high incidence and global prevalence of the disease in both developed and less developed nations. Inflammation plays a central role in CAD and pathogenshave been traditionally known to elicit a chronic systematic inflammatory response in the host (Danesh, Lancet 1997, 350; Hoffmeister, J. Am Coll Cardiol, 2000; 35-112).

Initial epidemiological studies have paved the way for direct experimental proof of association by looking for pathogens on serological samples (5-10) and by direct assessment of pathogen load using subgingival biofilm (Sphar, Arch Intern Med 2006; 166:554) or periodontal microbiota collected using sterile cuvettes (Desvarieux, Circulation 2005; 11:576) Fiehn J. Periodontal 2005; 76:731 detected the presence of DNA of periodontal pathogens, particularly *Prevotella intermedia*, but were unable to obtain live pathogens in culture. In a comprehensive ten year follow up of 6051 individuals from the FINRISK cohort (Pussinen, Atherosclerosis 2007; 193:222) has shown direct link between bacteria (Lipopolysaccharides—LPS) induced endotoxemia and systemic inflammation resulting in enhanced CVD risk. Subclinical endotoxemia has been previously shown to carry a e-fold elevated risk of incident atherosclerosis and CVD.

Two independent studies on S. American and Japanese population have shown the presence of *A. actinomycetemcomitans* in both dental plaques and cardiovascular specimens obtained from the same subjects using PCT based detection method (Padilla, J. Periodontal Res 2006; 41:350; Nakano Oral Microniol Immunol 2007; 78:677) while oral pathogens have been detected in atherosclerotic coronary tissue but not in internal mammary biopsy sample obtained during bypass procedure (Pucar, 2007 J. Periodontol 78:677). There have been several reports on significant association of periodontitis with ischemic stroke in men and young adults (Grau 2004; Stroke; U35:496), carotid atherosclerosis (Engerbretson 2005; Stroke; 36:561) as well as incident stroke (Pussinen et al 2007).

Association has also been shown between levels of IgG antibody titres to oral organisms, especially *Campylobacter rectus* and early sub-clinical atherosclerotic changes by way of measuring the carotid intima-media thickness assessed using B-mode ultrasound technique (Beck 2005; circulation; 112:19; Mustapaha 2007; J. Perodontol; 78:2289) Significant association was also observed between carotid plaque and radiographically assessed periodontal bone loss (Engebretson S P).

The immune response against oral pathogens is at least initially mediated by the mucosal immune system. The principal immunoglobulin involved is secretory IgA (Underdown and Mestecky, 1994). The antibody-forming plasma cell releases dimeric IgA, postranslationally associated with J chain. The J chain holds the two IgA molecules together and facilitates binding to the poly-Ig receptor expressed on the basal (distal) surface of epithelial cells. The complex is transported in endosomes to the luminal side of the epithelial cell and released into the secretions. The portion of the poly-Ig receptor retained with secreted IgA is called secretory component.

Secretory IgA prevents absorption of viruses, bacteria and toxins by blocking their adhesion to mucous membranes, enabling pathogens to be flushed away in the stream of secreted fluids or the mucociliary escalator of the respiratory tract. Antigen-specific IgA also neutralises viral pathogens during transport across "M" cells of Peyers patches, where nondegradative endosomal transport might otherwise deliver a pathogen into the host (Owen and Jones, 1974; Neutra and Kraehenbuhl, 1994, Mazanec, 1992).

IgA is the major immunoglobulin synthesised by the body, with 75 percent of plasma cells the antibody-producing cells in the body make IgA, most of which is released continuously into gastrointestinal fluid, saliva, tears, urine and other secretions.

Oral vaccination strategies targeting enteric diseases are well-known since the development of the Sabin oral poliomyelitis vaccine in the 1950s. In principle, the administration of antigen in immunogenic form via a mucosal route results in the production of antigen-specific secretory IgA, with or without the development of systemic tolerance. Classically vaccines contain antigens in the form of whole killed pathogens or live attenuated organisms, or in so-called sub-unit vaccines, purified or semi-purified antigens. In each case, adjuvants or other immunostimulatory components may be combined with the antigenic preparation to increase immunogenicity.

Following elucidation of the molecular basis of antigen presentation to T cells via the Class I and Class II major histocompatibiliy complex (MHC) pathways, more specific methods of delivering peptide antigens have been sought. Among these is the use of microsomal preparations from antigen-pulsed antigen-presenting cells, which, in principle, can deliver membrane-associated, MHC-bound peptides directly to appropriate T cells. One difficulty with this approach is that, as prepared by the usual methods, such microsomes usually contain MHC molecules oriented facing the lumen of the microsome rather than facing externally. To overcome this, 'inverted', or 'inside-out', microsomes, prepared by the use of repeated cycles of freeze-thawing of microsomal preparations has been suggested (International application WO2005/011730).

Many proteins from a variety of snake venoms have been identified as potent inhibitors of platelet aggregation and integrin-dependent cell adhesion. The majority of these proteins which belong to the so-called "disintegrin" family share a high level of sequence homology, are small (4-8 kDa), cysteine-rich and contain the sequence RGD (Gould R J et al (1990) Proc Soc Exp Biol Med 195: 168-171) or KGD (Scarborough R M et al (1991) J Biol Chem 266: 9359-9362). In addition to the disintegrin family, a number of non-disintegrin RGD proteins of similar inhibitory potency, high degree of disulfide bonding, and small size have been isolated from both the venoms of the Elapidae family of snakes (McDowell R S et al (1992) Biochemistry 31: 4766-4772; Williams J A et al (1992) Biochem Soc Trans 21: 73S) and from leech homogenates (Knapp A et al (1992) J Biol Chem 267: 24230-24234). All of these proteins are approximately 1000 times more potent inhibitors of the interactions of glycoprotein ligands with the integrin receptors than simple linear RGD peptides; a feature that is attributed to an optimally favourable conformation of the RGD motif held within the protein scaffold. The NMR structures of several inhibitors including kistrin (Adler M et al (1991) Science 253: 445-448; Adler M and Wagner G (1992) Biochemistry 31: 1031-1039; Adler M et al (1993) Biochemistry 32: 282-289), flavoridin (Senn H and Klaus W (1993) J Mol Biol 234: 907-925), echistatin (Saudek V et al (1991) Biochemistry 30: 7369-7372; Saudek V et al (1991) Eur J Biochem 202: 329-328; Cooke R M et al (1991) Eur J Biochem 202: 323-328; Cooke R M et al (1992) Protein Eng 5: 473-477), albolabrin (Jaseja M et al (1993) Eur J Biochem 218: 853-860), decorsin (Krezel A M et al (1994) Science 264: 1944-1947), and dendroaspin (Jaseja M et al (1994) Eur J Biochem 226: 861-868; Sutcliffe M J et al (1994) Nature Struct Biol 1: 802-807) have been reported, and the only common structural feature elucidated so far is the positioning of the RGD motif at the end of a solvent exposed loop, a characteristic of prime importance to their inhibitory action.

Dendroaspin, a short chain neurotoxin analogue containing the RGD sequence, and the disintegrin kistrin, which show little overall sequence homology but have similar amino acids flanking the RGD sequence (PRGDMP), are both potent inhibitors of platelet adhesion to fibrinogen but poor antagonists of the binding of platelets to immobilised fibronectin (Lu X et al (1994) Biochem J 304: 929-936). In contrast, elegantin, which has 65% sequence homology to kistrin but markedly different amino acids around RGD (ARGDNP), preferentially inhibited platelet adhesion to fibronectin as opposed to fibrinogen and binds to an allosterically distinct site on the $\alpha_{IIb}\beta_3$ complex.

Smith J W et al (1995) Journal of Biological Chemistry 270: 30486-30490 undertook protein "loop grafting" experiments to construct a variant of tissue-type plasminogen activator (t-PA) which bound platelet integrin $\alpha_{IIb}\beta_3$. Amino acids in a surface loop of the epidermal growth factor (EGF) domain of t-PA were replaced with residues from a complementarity-determining region (CDR) forming one CDR of a monoclonal antibody reactive against the adhesive integrin receptor $\alpha_{IIb}\beta_3$. The resulting variant of t-PA (loop-grafted-t-PA) bound $\alpha_{IIb}\beta_3$ with nanomolar affinity and had full activity to both synthetic and natural substrates. The effects and applicability of loop grafting are altogether unpredictable and uncertain.

The dendroaspin scaffold lends itself to modification. When dendroaspin (including the RGD motif) is modified to incorporate further functional amino acid sequences eg active portions or motifs of agonists, antagonists or inhibitors of factors in the clotting cascade, the resulting molecules are particularly useful as anticoagulants and do not suffer from the drawbacks associated with existing anticoagulants (see International application WO 01/57210). Such hybrid polypeptides may comprise a first amino acid sequence including the RGD motif and conferring dendroaspin activity and a further amino acid sequence conferring activity other than that of dendroaspin activity. In this way the hybrid dendroaspin-based molecules may be rendered multifunctional so that they are active against, for example, platelet aggregation, as well as one or more further component in the clotting cascade (eg thrombin activity), or the intracellular signalling cascade (eg growth factor).

Oral compositions, formulated as a toothpaste, for treating microbial infection are disclosed in US2003014909.

Statement of Invention

In a first aspect the invention provides a recombinant protein comprising:
i) a carrier portion;
ii) a first epitope capable of eliciting an anti-atheroma response; and
iii) a second epitope capable of eliciting an anti-atheroma response,
characterised in that said first and second epitopes are distinct from one another.

Preferably said first epitope is capable of eliciting an immune response against a polypeptide selected from the group consisting of: an apolipoprotein, a platelet derived growth factor, a heat-shock protein, an oxidised LDL, Cholesteryl ester transfer protein and a β2-Glycoprotein I. Alternatively said first epitope is capable of eliciting an immune response against a pathogen selected from the group consisting of: human cytomegalovirus, *chlamydia pneumonia*, *porphyromonas gingivalis* or *streptococcus pneumoniae*.

Preferably said second epitope is capable of eliciting an immune response against a polypeptide selected from the group consisting of: a heat-shock protein, a platelet derived growth factor, an oxidised LDL, a β2-Glycoprotein I, Cholesteryl ester transfer protein and an apolipoprotein. Alternatively said second epitope is capable of eliciting an immune response against a pathogen selected from the group consisting of: human cytomegalovirus, *chlamydia pneumonia*, *porphyromonas gingivalis*, *streptococcus pneumoniae*.

Preferably said apolipoprotein (Apo) is an ApoB1 or an ApoB2. More preferably, said epitope capable of eliciting a response against Apob1 is a polypeptide comprising the amino acid sequence of SEQ ID NO: 25. Preferably said epitope capable of eliciting a response against Apob2 is a polypeptide comprising the amino acid sequence of SEQ ID NO: 38.

Preferably, said heat-shock protein (HSP) is a HSP 60 or a HSP 65. More preferably said HSP 60 is a human HSP 60 or a *Mycobacterium bovis* HSP. More preferably said epitope capable of eliciting a response against HSP 60 is a polypeptide comprising the amino acid sequence of any one of SEQ ID NO: 9 to 21, 26, 28, 29 or 33.

Preferably, said epitope capable of eliciting a response against platelet derived growth factor (PDGF) is a polypeptide comprising the amino acid of any one of SEQ ID NO:1 to 9 or 22.

Preferably, said epitope capable of eliciting a response against Cholesteryl ester transfer protein (CETP) is a polypeptide comprising the amino acid of SEQ ID NO:39.

Preferably, said epitope capable of eliciting a response against human cytomegalovirus (hCMV) is a polypeptide comprising the amino acid of any one of SEQ ID NO:30 or 24.

Preferably, said chlamydia pneumonia is Cpn1 or Cpn2. More preferably, said epitope capable of eliciting a response against Cpn1 is a polypeptide comprising the amino acid of SEQ ID NO: 37. Preferably, said epitope capable of eliciting a response against Cpn2 is a polypeptide comprising the amino acid of SEQ ID NO: 38.

Preferably, said epitope capable of eliciting a response against *porphyromonas gingivalis* is a polypeptide comprising the amino acid of any one of SEQ ID NO:32 or 34. Preferably said epitope capable of eliciting a response against *streptococcus pneumoniae* is a polypeptide comprising the amino acid of any one of SEQ ID NO:23.

More preferably said first epitope is capable of eliciting an immune response against ApoB1 and said second epitope is capable of eliciting a response against human cytomegalovirus.

Preferably said carrier protein is a dendroaspin scaffold. Alternatively, said carrier protein is a keyhole limpet hemocyanin (KLH).

Preferably said first epitope is inserted into dendroaspin loop II and said second epitope is inserted into dendroaspin loop III.

Preferably said dendroaspin scaffold comprises a first epitope capable of eliciting a response to a PDGF loop I peptide and a second epitope capable of eliciting a response to a cytomegalovirus pp 65 peptide. More preferably, said dendroaspin scaffold comprises SEQ ID NO: 22 inserted into dendroaspin loop II and SEQ ID NO: 27 inserted into dendroaspin loop III. Alternatively, said dendroaspin scaffold comprises a first epitope capable of eliciting a response to a PDGF loop I peptide and a second epitope capable of eliciting a response to a *Mycobacterium bovis* hsp60 peptide. Preferably, said dendroaspin scaffold comprises SEQ ID NO: 22 inserted into dendroaspin loop II and any one of SEQ ID NOS 9-21 inserted into dendroaspin loop III. More preferably, said dendroaspin scaffold comprises SEQ ID NO: 22 inserted into dendroaspin loop II and SEQ ID NO: 26 inserted into dendroaspin loop III. Alternatively, said dendroaspin scaffold comprises a first epitope capable of eliciting a response to a PDGF loop III peptide and a second epitope capable of eliciting a response to a peptide mimotope of a *Streptococcus pneumoniae* capsular polysaccharide. Preferably said peptide mimotope is a peptide mimotope of a type 8 *Streptococcus pneumoniae* capsular polysaccharide. More preferably, said dendroaspin scaffold comprises SEQ ID NO: 1 inserted into dendroaspin loop II and SEQ ID NO: 23 inserted into dendroaspin loop III.

Still more preferably, the recombinant protein of the invention comprises a third epitope capable of eliciting an anti-atheroma response, wherein said third epitope is distinct from said first and second epitopes. More preferably, the recombinant protein comprises a fourth epitope capable of eliciting an anti-atheroma response, wherein said fourth epitope is distinct from said first, second and third epitopes.

In a further aspect there is provided an expression vector comprising a nucleic acid molecule encoding a recombinant polypeptide according to the invention.

In a further aspect there is provided an immunogenic composition comprising the recombinant protein according to the invention and an immunogenic hydrophobic complex. Preferably, the immunogenic hydrophobic complex comprises an isolated microsome. Preferably the immunogenic composition comprises an MHC protein. Preferably, the microsome is an inverted microsome.

In a further aspect there is provided a pharmaceutical composition comprising an immunogenic composition of the invention, formulated as a gel, oromucosal paste, toothpaste or mouthwash. Preferably, the pharmaceutical composition comprises one or more constituents selected from the list consisting of gelatin, pectin, sodium carboxymethylcellulose, polyethylene resin and liquid paraffin.

In a further aspect there is provided a pharmaceutical composition comprising the recombinant protein according to the invention, the vector according to the invention or the immunogenic composition according to the invention.

In a further aspect there is provided the recombinant protein according to the invention or the vector according to the invention for use as a medicament.

In a further aspect there is provided a method of eliciting an anti-atheroma response in a mammal comprising administering the recombinant protein according to the invention, the vector according to the invention, the immunogenic composition according to the invention or the pharmaceutical composition according to the invention.

In a further aspect there is provided a method of treating or preventing atheroma comprising administering to an individual in need thereof a therapeutically acceptable amount of the recombinant protein according to the invention, the vector according to according to the invention, the immunogenic composition according to the invention or the pharmaceutical composition according to the invention.

In a further aspect there is provided an anti-atheroma vaccine comprising the recombinant protein according to the invention or the vector according to the invention.

In a further aspect there is provided a process for inducing secretory immunoglobulins on mucosal surfaces of a mammal or human, comprising administering to the mammal or human the immunogenic composition in accordance with the invention. Preferably, the administration involves multiple dosages of the immunogenic composition over time.

In a further aspect there is provided a method of eliciting an immune response against one or more epitope of interest comprising
  a. constructing and expressing a dendroaspin scaffold protein comprising said one or more epitope of interest
  b. incubating eukaryotic cells with said dendroaspin scaffold protein
  c. using said eukaryotic cells to prepare microsomes
  d. incorporating said microsomes and dendroaspin scaffold protein with one or more pharmaceutically-acceptable constituents to produce an orally administrable preparation
  e. administering said preparation to a mammal or human orally.

Sequences

The Sequence Listing is submitted as an ASCII text file named "86080-01_ST25.txt," created on Nov. 1, 2012, ~8.5 KB, which is incorporated by reference herein.

DETAILED DESCRIPTION OF THE INVENTION

The invention is described in detail with reference to the following figures.

FIG. 1 shows a schematic structure of the peptide backbone of dendroaspin and its three exposed loops.

Figure 2:
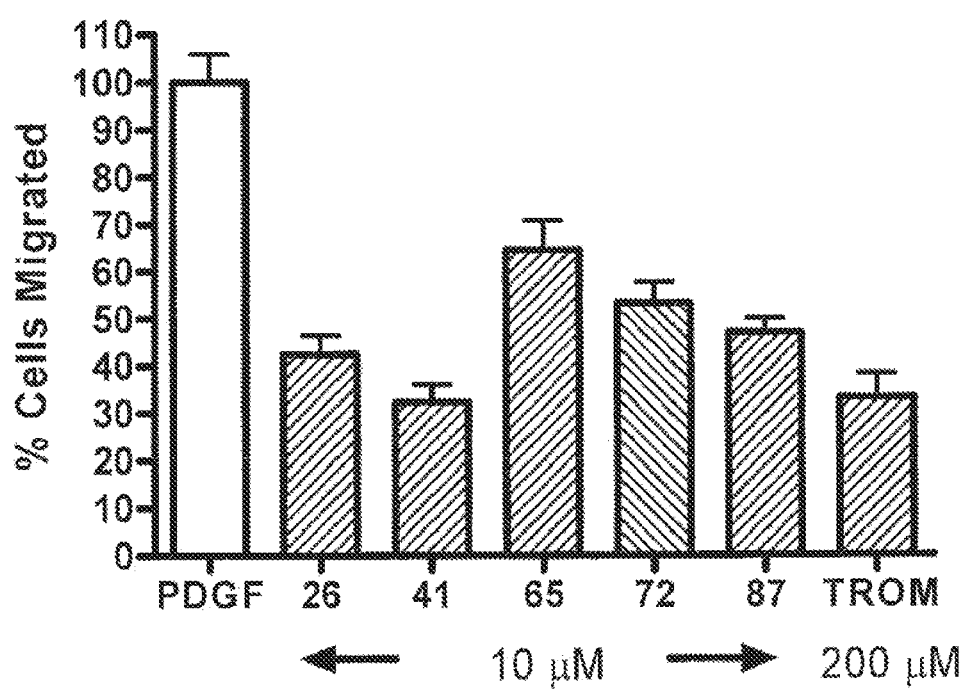

FIG. 2 shows the results of a cell migration inhibition assay comparing clones 26, 41, 65, 72 and 87 (at 10 µM) and a cyclic PDGF loop 1 peptide (cPDGF) at 200 µM, all competing with PDGF at 20 ng ml$^{-1}$ See Results, section 3-a.

Figure 3:
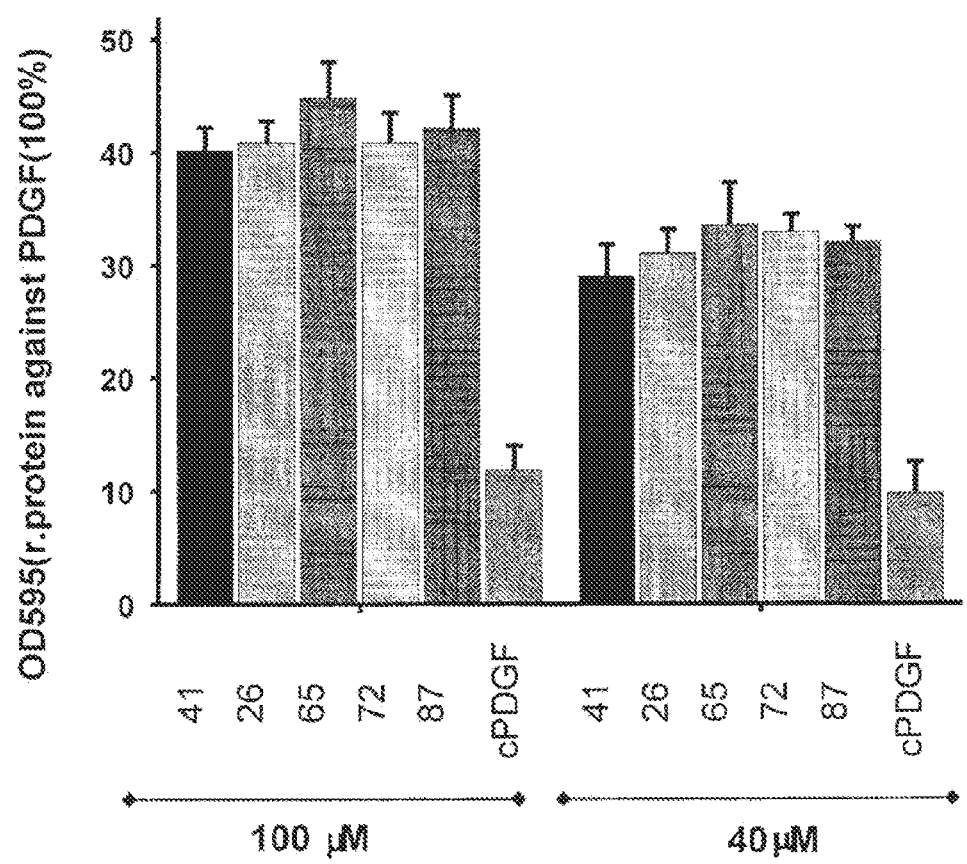

FIG. 3 shows the inhibitory effect of clones 26, 41, 65, 72 and 87 and a cyclic PDGF loop 1 peptide (cPDGF) (at 100 µM and 40 µM) on PDGF-induced cell proliferation. See section 3-b.

Figure 4A:
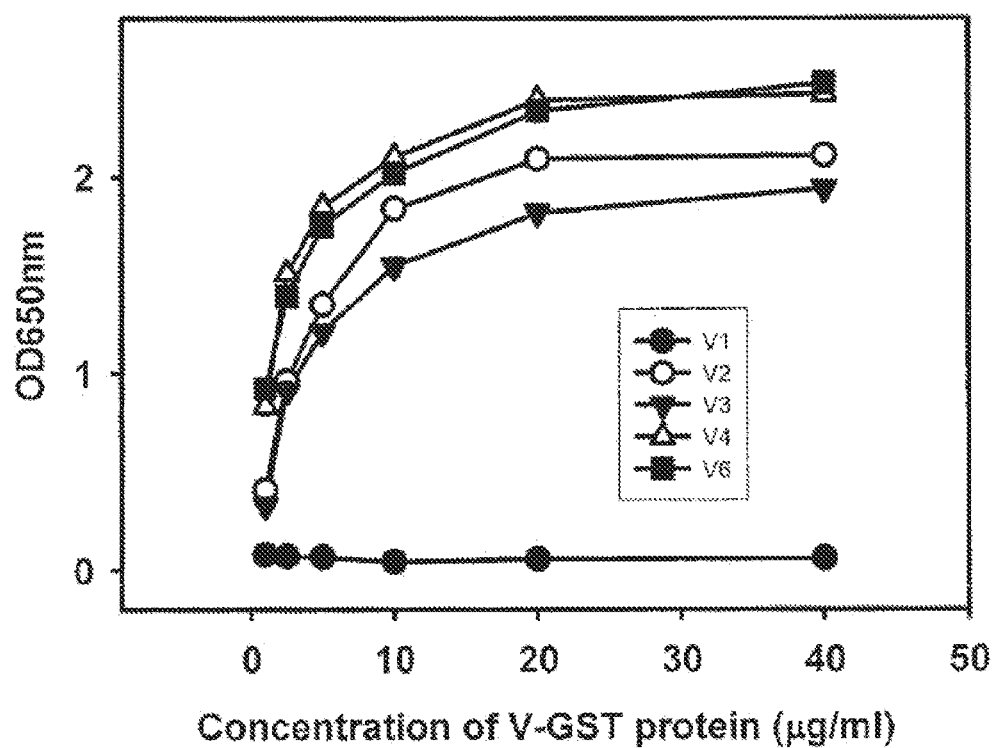
Figure 4B:
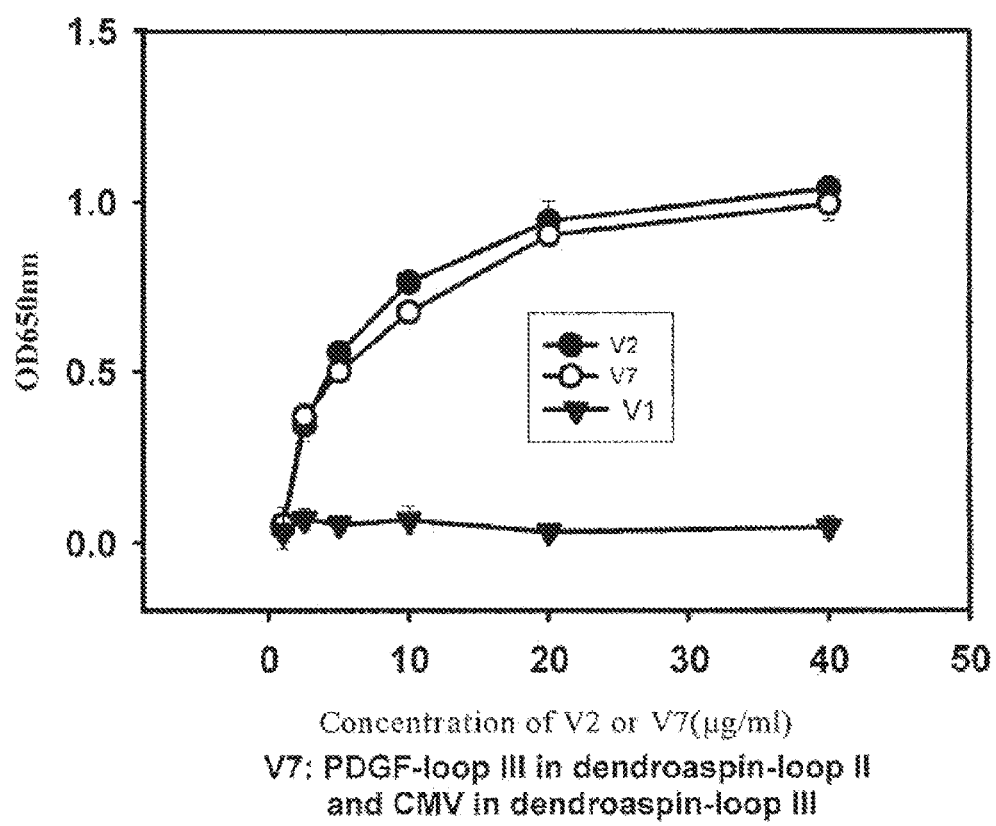

FIG. 4 demonstrates the immunoreactivity of various constructs. FIG. 4A titrates recombinant protein constructs V1, 2, 3, 4 and 6 against anti-PDGF BB polyclonal antibody. FIG. 4B titrates constructs V1, 2 and 7 against an anti-*Streptococcus pneumoniae* polyclonal antibody (produced by *Streptococcus pneumoniae* vaccine). See section 3-c.

Figure 5:
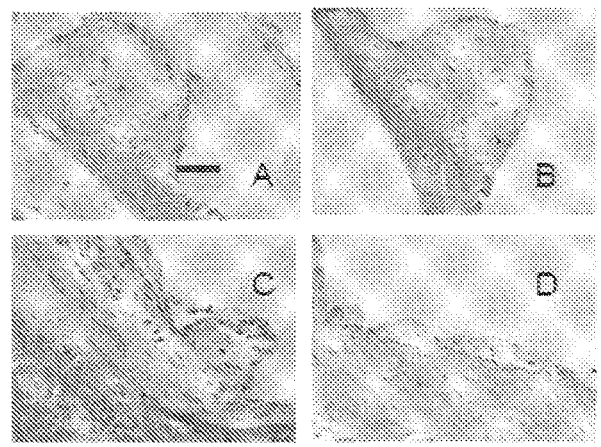

FIG. 5 shows Lesion of atherosclerosis analysed with elastin/van Gieson staining in aortas from adjuvant control mouse (A) and mice immunised with Apo B (B), hHSP (C) and Apo B+HSP (D) peptides. (A, scale bar indicates 20 µm). Compared to adjuvant control, immunization with Apo B or HSP reduced atherosclerotic lesions (14.66% and 22.15%, respectively). Immunization with Apo B plus HSP reduced significantly atherosclerotic lesions (41.34%, p=0.0254).

Figure 6:
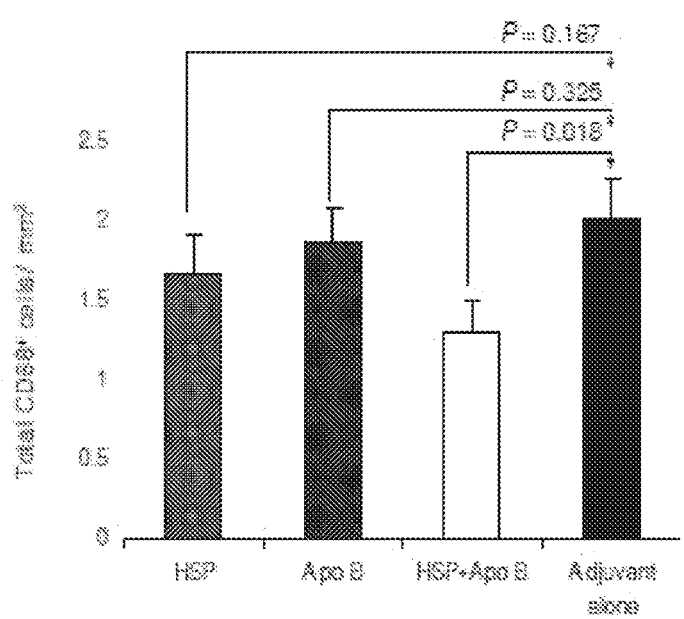

FIG. 6 shows the total number of CD68+ cells (cells/mm$^2$) in the lesions of atherosclerosis in mice immunized with HSP, ApoB, HSP+ApoB and adjuvant alone.

Figure 7:
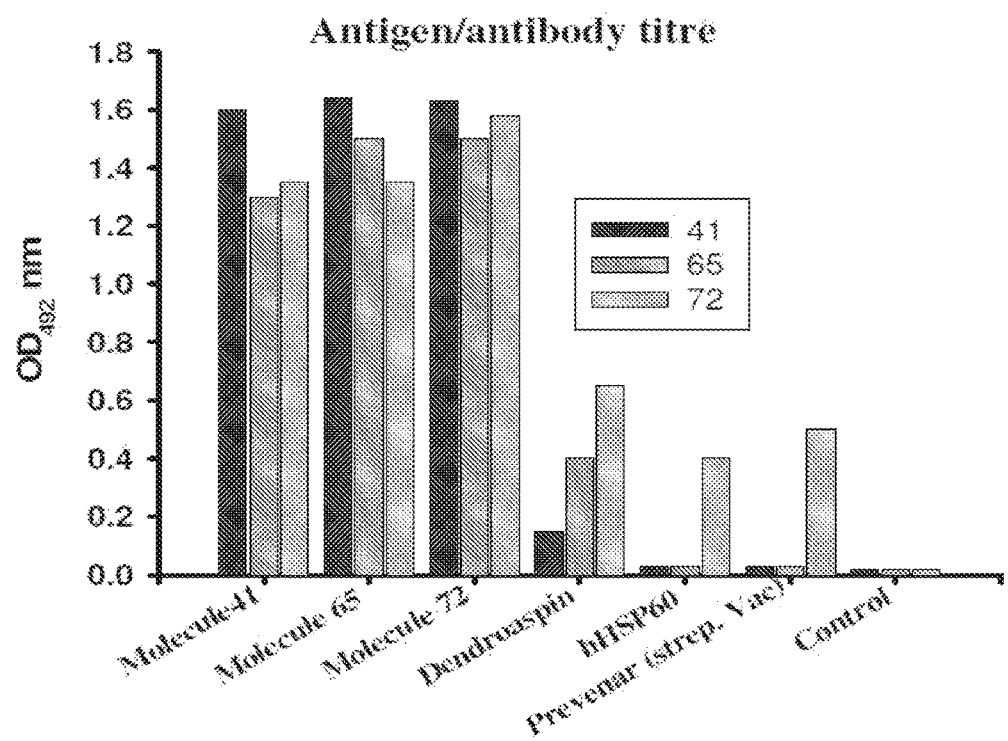

FIG. 7 shows Antigen-antibody titre using immunized mice anti-sera after 9 weeks since injection at 0 time point 1st inoculation 10 µg protein+Alum; 3 week time point, 2nd inoculation 10 µg protein+complete Freund's adjuvant; 5 week time point, 3rd inoculation 10 µg protein+incomplete.

Figure 8:
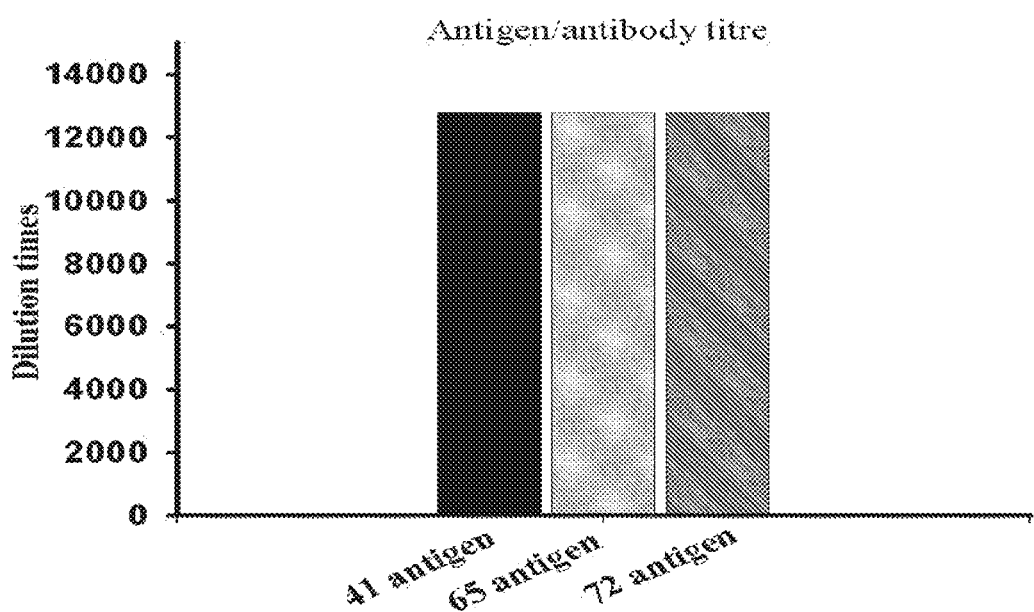

FIG. 8 Antigen-antibody titre at 12800 times dilution. Antigen (41, 65 and 72) was coated on to a plate and anti-sera of each antigen was used as polyclonal antibody for the titration.

In one aspect the invention provides an expression vector comprising an expressible nucleic acid encoding the one of the recombinant proteins herein described. The vector may be any vector capable of transferring DNA to a cell. Preferably, the vector is an integrating vector or an episomal vector.

Preferred integrating vectors include recombinant retroviral vectors. A recombinant retroviral vector will include DNA of at least a portion of a retroviral genome which portion is capable of infecting the target cells. The term "infection" is used to mean the process by which a virus transfers genetic material to its host or target cell. Preferably, the retrovirus used in the construction of a vector of the invention is also rendered replication-defective to remove the effect of viral replication of the target cells. In such cases, the replication-defective viral genome can be packaged by a helper virus in accordance with conventional techniques. Generally, any retrovirus meeting the above criteria of infectiousness and capability of functional gene transfer can be employed in the practice of the invention.

Suitable retroviral vectors include but are not limited to pLJ, pZip, pWe and pEM, well known to those of skill in the art. Suitable packaging virus lines for replication-defective retroviruses include, for example, ΨCrip, ΨCre, Ψ2 and ΨAm. Particularly suitable retroviral vectors are lentiviral vectors, especially HIV, SIV and FIV.

Other vectors useful in the present invention include adenovirus, adeno-associated virus, SV40 virus, vaccinia virus, HSV and poxvirus vectors. A preferred vector is the adenovirus. Adenovirus vectors are well known to those skilled in the art and have been used to deliver genes to numerous cell types, including airway epithelium, skeletal muscle, liver, brain and skin (Hitt et al, 1997 Advances in Pharmacology 40: 137-206; Anderson, 1998 Nature 392: (6679 Suppl): 25-30) and to tumours (Mountain, 2000 Trends Biotechnol 18: 119-128).

A further preferred vector is the adeno-associated (AAV) vector. AAV vectors are well known to those skilled in the art and have been used to stably transduce human T-lymphocytes, fibroblasts, nasal polyp, skeletal muscle, brain, erythroid and haematopoietic stem cells for gene therapy applications (Philip et al, 1994 Mol Cell Biol 14: 2411-2418; Russell et al, 1994 Proc Natl Acad Sci USA 91: 8915-8919; Flotte et al, 1993 Proc Natl Acad Sci USA 90: 10613-10617; Walsh et al, 1994 Proc Natl Acad Sci USA 89:7257-7261; Miller et al, 1994 Proc Natl Acad Sci USA 91:10183-10187.; Emerson, 1996 Blood 87, 3082-3088). International Patent Application WO 91/18088 describes specific AAV-based vectors.

Preferred episomal vectors include transient non-replicating episomal vectors and self-replicating episomal vectors with functions derived from viral origins of replication such as those from EBV, human papovavirus (BK) and BPV-1.

Such integrating and episomal vectors are well known to those skilled in the art and are fully described in the body of literature well known to those skilled in the art. In particular, suitable episomal vectors are described in WO98/07876.

Mammalian artificial chromosomes can also be used as vectors in the present invention. The use of mammalian artificial chromosomes is discussed by Calos (1996 Trends in Genetics 12: 463-466).

In a preferred embodiment, the vector of the present invention is a plasmid. The plasmid may be is a non-replicating, non-integrating plasmid.

The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures.

A non-replicating, non-integrating plasmid is a nucleic acid which when transfected into a host cell does not replicate and does not specifically integrate into the host cell's genome (i.e. does not integrate at high frequencies and does not integrate at specific sites).

Replicating plasmids can be identified using standard assays including the standard replication assay of Ustav et al (1991 EMBO J 10: 449-457).

The present invention also provides a host cell transfected with the vector of the present invention. The host cell may be any mammalian cell. Preferably the host cell is a rodent or mammalian cell.

Numerous techniques are known and are useful according to the invention for delivering the vectors described herein to cells, including the use of nucleic acid condensing agents, electroporation, complexing with asbestos, polybrene, DEAE cellulose, Dextran, liposomes, cationic liposomes, lipopolyamines, polyornithine, particle bombardment and direct microinjection (reviewed by Kucherlapati and Skoultchi (1984 Crit. Rev. Biochem 16: 349-379); Keown et al (1990 Methods Enzymol 185:527-37).

A vector of the invention may be delivered to a host cell non-specifically or specifically (i.e., to a designated subset of host cells) via a viral or non-viral means of delivery. Preferred delivery methods of viral origin include viral particle-producing packaging cell lines as transfection recipients for the vector of the present invention into which viral packaging signals have been engineered, such as those of adenovirus, herpes viruses and papovaviruses. Preferred non-viral based gene delivery means and methods may also be used in the invention and include direct naked nucleic acid injection, nucleic acid condensing peptides and non-peptides, cationic liposomes and encapsulation in liposomes.

The direct delivery of vector into tissue has been described and some short-term gene expression has been achieved. Direct delivery of vector into muscle (Wolff et al, 1990 Science 247: 1465-1468), thyroid (Sikes et al, 1994 Human Gene Therapy 5: 837-844), melanoma (Vile et al, 1993 Cancer Res 53: 962-967), skin (Hengge et al (1995. Nature Genet 10: 161-166), liver (Hickman et al (1994 Human Gene Therapy 5: 1477-1483.) and after exposure of airway epithelium (Meyer et al, 1995) is clearly described in the prior art.

Various peptides derived from the amino acid sequences of viral envelope proteins have been used in gene transfer when co-administered with polylysine DNA complexes (Plank et al, 1994 J Biol Chem 269: 12918-12924; Trubetskoy et al, 1992 Bioconjugate Chem 3: 323-327; WO 91/17773; WO 92/19287; and Mack et al, 1994 Am J Med Sci 307: 138-143) suggesting that co-condensation of polylysine conjugates with cationic lipids can lead to improvement in gene transfer efficiency. International Patent Application WO 95/02698 discloses the use of viral components to attempt to increase the efficiency of cationic lipid gene transfer.

Nucleic acid condensing agents useful in the invention include spermine, spermine derivatives, histones, cationic peptides, cationic non-peptides such as polyethyleneimine (PEI) and polylysine. 'Spermine derivatives' refers to analogues and derivatives of spermine and include compounds as set forth in International Patent Application WO 93/18759 (published Sep. 30, 1993).

Disulphide bonds have been used to link the peptidic components of a delivery vehicle (Cotten et al, 1992 Meth Enzymol 217: 618-644). See also Trubetskoy et al. (supra).

Delivery vehicles for delivery of DNA constructs to cells are known in the art and include DNA/polycation complexes which are specific for a cell surface receptor, as described in, for example, Wu and Wu (1988 J Biol Chem 263:14621), Wilson et al (1992. J Biol Chem 267:963-967) and U.S. Pat. No. 5,166,320.

Delivery of a vector according to the invention is contemplated using nucleic acid condensing peptides. Nucleic acid condensing peptides, which are particularly useful for condensing the vector and delivering the vector to a cell, are described in International Patent Application WO 96/41606. Functional groups may be bound to peptides useful for delivery of a vector according to the invention, as described in WO 96/41606. These functional groups may include a ligand that targets a specific cell-type such as a monoclonal antibody, insulin, transferrin, asialoglycoprotein, or a sugar. The ligand thus may target cells in a non-specific manner or in a specific manner that is restricted with respect to cell type.

The functional groups also may comprise a lipid, such as palmitoyl, oleyl, or stearoyl; a neutral hydrophilic polymer such as polyethylene glycol (PEG), or polyvinylpyrrolidine (PVP); a fusogenic peptide such as the HA peptide of influenza virus; or a recombinase or an integrase. The functional group also may comprise an intracellular trafficking protein such as a nuclear localisation sequence (NLS), an endosome escape signal such as a membrane disruptive peptide, or a signal directing a protein directly to the cytoplasm.

Also provided is a method of eliciting an anti-atheroma immune response in a mammal comprising administering the recombinant protein or expression vector herein described and an anti-atheroma vaccine comprising the protein or expression vector.

Also provided is a method of treating or preventing atheroma comprising administering to an individual requiring such treatment a therapeutically effective amount of the recombinant protein or expression vector herein described.

The invention provides a recombinant protein scaffold/carrier molecule. Preferably the scaffold comprises one or more inserted non-carrier/scaffold epitopes; that is, amino acid sequences from other proteins. Such sequences may be conveniently inserted by means of recombinant DNA technology or through artificial peptide synthesis. Preferably the carrier/scaffold molecule comprises two or more inserted non-carrier/scaffold epitopes, alternatively three or more, or four or more inserted non-carrier epitopes. Preferably the carrier is a dendroaspin scaffold.

In one aspect the immunogenic composition of the invention comprises a dendroaspin molecule comprising one or more epitopes from proteins in the list consisting of human hsp60, *M. bovis* hsp 60, hsp65, *Porphyromonas gingivalis* hsp, PDGF, oxLDL, cytomegalovirus protein pp 65, ApoB and CETP, or a peptide mimotope of a *Streptococcus pneumoniae* polysaccharide. Preferably the dendroaspin molecule comprises one or more of SEQ ID NOs 1 to 33, preferably it comprises one or more of SEQ ID NOs 1, 9, 10, 11, 12, 13, 14, 15, 16, 17, 18, 19, 20, 21, 22, 23, 24, 26, 27, 28, 29, 30, 31, 32, or 33; more preferably it comprises one of the constructs shown in Table 3.

Also provided is a vaccine composition comprising any of the abovementioned immunogenic compositions together with one or more pharmaceutically acceptable excipients. Preferably the vaccine composition is an oral vaccine composition.

An effective vaccine against atheroma and atherosclerosis can be developed by combining an antibody reactive against atherosclerosis-linked autoimmune antigens (molecular mimics of infective agents or neoantigens) and an antibody capable of neutralising the growth factor and chemotactic action of PDGF. In particular, a protein moiety that binds both a heat shock protein and a atheroma-associated molecule such as PDGF, or a foam cell-specific antigen, acts as to enhance an anti-atheroma immune response. In principle, any molecule capable of such bispecific binding may be used as the basis of enhancing or initiating such a therapeutic or prophylactic immune response but one convenient approach is to engineer a recombinant protein with protein binding domains capable of binding both a heat shock protein and an atheroma-associated antigen. One particularly useful embodiment of this concept is a recombinant bispecific antibody molecule capable of binding both targets. Such a bispecific antibody may also, of course, be produced by direct chemical combination of separate purified monospecific antibodies.

Without being bound by any one theory or mechanism, it may be that some heat shock proteins act to target the complex of anti-atheroma target antigen, bispecific binding protein and heat shock protein to antigen presenting cells, particularly dendritic cells, by binding to a specific receptor (CD91) and so such a bispecific binding protein or antibody is particularly effective in eliciting an anti-atheroma immune response.

Also included within the present invention is a recombinant protein comprising a first portion capable of binding to a heat shock protein and a second portion capable of eliciting an anti-atheroma immune response. Preferably said second portion is capable of eliciting anti-PDGF immune response and more preferably said second portion comprises a PDGF-binding domain. Alternatively, said second domain is capable of eliciting an anti-foam cell immune response, preferably it comprises a foam cell antigen-binding domain. Preferably the first portion of said protein is capable of binding to hsp60 or hsp65. In a particularly preferred embodiment the protein comprises a bispecific antibody or bispecific functional fragment thereof.

Also included within the present invention is a recombinant protein comprising a first portion capable of binding to a heat shock protein and a second portion comprising a PDGF-derived immunogenic epitope. Alternatively said second portion comprises an immunogenic epitope from a foam cell antigen. Preferably said recombinant protein is an antibody or functional fragment thereof comprising one or more antigen-binding sites specific for the heat shock protein, and which also comprises one or more epitopes specific for an atheroma-associated antigen such as PDGF or a foam cell-specific antigen encoded in a some other, non-antigen binding, part of the antibody.

Development of a Bispecific Vaccine
1) Selection of PDGF Epitopes
1-a) Peptide Sequences Used in the Development of Atherovax.

A series of peptides corresponding to residues in loops I and III of PDGF-BB were prepared at the Institute as antigens in the development of Atherovax (Oefner et al, EMBO J 1992, 11, 3921-3926; Sun et al, Annu Rev Biophys Biomol Struct 1995, 24, 269-291; LaRochelle et al, J Biol Chem 1992, 267, 17074-17077; Brennand et al, FEBS Lett 1997, 413, 70-74; Patel et al, J Pept Res, 1999, 53, 68-74). In addition, certain of the peptides were shown to stimulate DNA synthesis in dermal fibroblasts. Based upon these a series of cyclic peptides was also prepared, one of which was capable of inhibiting PDGF-induced DNA synthesis and of inducing apoptosis. The cyclic peptide showed a correlation between its ability to inhibit cellular proliferation and the presence of PDGF receptors on cells.

1-b) General Methods for Peptide Synthesis.

Peptides are synthesised by continuous-flow solid-phase synthesis using the Fmoc strategy. N-terminal blocking is performed using 45% acetic anhydride in N,N-dimethyl-formamide for 30 min prior to cleavage and deprotection. Cyclisation of peptides is carried out on line using allyl-based protection of Glu. Following removal of the N-Fmoc group, head to tail cyclisation is performed using O-(7 azabenzotriazol-1-yl)-1,1,3,3-tetramethyluronium hexafluorophosphate and 1-hydroxy-7-azabenzotrizole as per manufacturer's instructions. Peptides are purified by reverse-phase HPLC on a Vydac C18 column (22×250 mm) using a 30 min gradient of 10-60% acetonitrile in 0.1% trifluoroacetic acid. Identification and characterisation of the purified peptides is performed using analytical reverse-phase HPLC and ESI mass-spectrometry. Examples of peptide sequences and defined peptide numbers synthesised are given in Table 1.

TABLE 1

Peptides used in development of anti-PDGF antibodies

| Peptide Number | Structure | SEQ ID No |
|---|---|---|
| 1 | $^{73}$RKIEIVRKK$^{81}$ | 1 |
| 2 | Ac-$^{73}$RKIEIVRKK$^{81}$ | 2 |
| 3 | Ac-$^{73}$RKIEIVRKK$^{81}$-MH$_2$ | 3 |
| 4 | $^{73}$RKIEIVRKK$^{81}$-C | 4 |
| 5 | Ac-$^{73}$RKIEIVRKK$^{81}$-C | 5 |
| 6 | $^{77}$IVRKR$^{81}$-C-$^{73}$RKIE$^{76}$ | 6 |
| 7 | $^{77}$IVRKK$^{81}$-C-$^{73}$RKIE$^{76}$ | 7 |
| 8 | GC-$^{25}$ISRRLIDRTNANFL$^{38}$-CG | 8 |
| | $^{25}$ISRRLIDRTNANFL$^{38}$ (PDGF) | 22 |

2) Selection of HSP65 Epitopes

Pioneering studies by Wick and colleagues (Wick et al, Immunol Today. 1995, 16, 27-33) have demonstrated antibody responses and cell-mediated immune reactivity to HSP65/60 in human and experimental atherosclerosis. In contrast to oxLDL, parenteral immunisation with HSP65 aggravates atherosclerosis (Xu et al, Arterioscl Thromb. 1992, 12, 789-799) and the transfer of HSP65-reactive cells also accelerates disease in hypercholesterolemic animal models Shoenfeld et al, J Autoimmun. 2000, 15, 199-202). Recent work suggests that the human HSP60 and bovis HSP65 (Uray et al, Int Immunol. 2003, 15, 1229-1236) may possess epitopes responsible for pathogenicity, as well as conferring resistance to disease induction, eg in arthritis (Ulmansky et al, J Immunol. 2002, 168, 6463-6469) and atherosclerosis (Perschinka et al, Arterioscler Thromb Vasc Biol. 2003, 23, 1060-1065). The epitopes of human HSP60 and bovis HSP65 have been tested for their antigenicities. The epitope selection was based on protein segments with a high probability of β-turn secondary structure and a low probability of hydrophobicity (Uray et al, Int Immunol. 2003, 15, 1229-1236). Examples of peptide sequences and defined peptide numbers to be synthesised are given in Table 2.

TABLE 2

*Mycobacterium bovis* Hsp60 peptides

| hsp60 peptide | SEQ ID NO |
|---|---|
| $^{31}$PKGRNVVLEK$^{40}$ | SEQ ID NO: 9 |
| $^{91}$TVLAQALVRE$^{100}$ | SEQ ID NO: 10 |
| $^{141}$QIAATAAISA$^{150}$ | SEQ ID NO: 11 |
| $^{191}$RFDKGYISGY$^{200}$ | SEQ ID NO: 12 |
| $^{196}$YISGYFVTDP$^{205}$ | SEQ ID NO: 13 |
| $^{201}$FVTDPERQEA$^{210}$ | SEQ ID NO: 14 |
| $^{216}$YILLVSSKVS$^{225}$ | SEQ ID NO: 15 |
| $^{276}$PGFGDRRKAM$^{285}$ | SEQ ID NO: 16 |
| $^{281}$RRKAMLQDMA$^{290}$ | SEQ ID NO: 17 |
| $^{366}$LAKLAGGVAV$^{375}$ | SEQ ID NO: 18 |
| $^{413}$GVTLLQAAPT$^{422}$ | SEQ ID NO: 19 |
| $^{502}$NAASIAGLFL$^{511}$ | SEQ ID NO: 20 |
| $^{507}$AGLFLTTEAV$^{516}$ | SEQ ID NO: 21 |

3) Initial Results of Vaccine Constructs 3-a) Expression of Recombinant Dendroaspin Scaffold Immunogens A number of recombinant immunogens comprising a dendroaspin scaffold with PDGF and/or *Streptococcus pneumoniae*, CMV, ApoB, or *M. bovis* hsp60-derived peptides grafted into loops 2 and/or 3 (as shown in Table 3) were generated. The dendroaspin molecule provides a useful scaffold on which to graft peptide sequences. It has three exposed loops (see FIG. 1), which allow expression and presentation of grafted peptide sequences. Such recombinant chimeric dendroaspin constructs are conveniently expressed as glutathione S-transferase fusion proteins in prokaryotic expression systems according to standard methodology.

Expression of Proteins

Expression of recombinant proteins was carried out as described previously (Lu et al, 2001; BJ). Briefly, A 500 ml culture (2YT medium plus 100 μg/ml ampicillin final concentration) was inoculated with 1 ml of seed culture. The culture was grown over night with shaking (250 rpm) at 37° C. 1 litre of fresh 2YT$^{amp}$ was added and the culture incubated for a further 3 h at 37° C. IPTG was added to a final concentration of 0.1 mM and the culture was incubated at 30° C. for an additional 4 h prior to sedimentation in a Sorvall (GS-3) rotor at 4° C. (6000 rpm 15 min). Pellets were stored at −20° C.

Protein Purification

Affinity Purification:

GST-recombinant protein was purified from the supernatant of sonicated cells after centrifugation by affinity chromatography, using glutathione-Sepharose 4B columns. Glutathione Sepharose 4B is designed for rapid single step purification of recombinant derivatives of glutathione S-transferase or other glutathione dependent proteins. Cells were dissolved in PBS with the following inhibitors: trypsin inhibitor (50 mg/ml), pepstatin (10 mg/ml), aprotinin (10 ml stock), EDTA (0.5 M) and PMSF (100 mM in EtOH). After sonication (sonicated 4 times on ice, 50 seconds each time for 30 ml volume of cell mixture) 10% Triton-X 100 solution was added and left on ice for 10 min. Centrifugation was carried out at 16,000×g for 30 min using Rotor SS-34 on Sorvall RC-5B centrifuge. The supernatant was then collected and loaded on to the purification column. The column was washed with PBS and Tris-HCl (pH 8.0) buffer. Proteins were eluted with buffer containing 50 μM Glutathione. Peak levels of protein product were collected, pooled and mutant-ADAMs were released from GST-fusion proteins by digestion with factor Xa (1:300, w/w, Factor Xa: fusion protein) at 4° C. for 12 hours. The product was purified by reverse-phase HPLC.

HPLC Purification:

After Factor Xa cleavage, the fractions were loaded onto a Vydac $O_{18}$ reverse phase HPLC analytical column (TP104) and eluted with a gradient of 0-26% acetonitrile (1.78% per min) containing 0.1% TFA, followed by 26-36% acetonitrile in 0.1% TFA (0.25% per min). Active fractions were identified by a functional assay and were re-chromatographed to homogeneity. Purified proteins were originally verified by mass spectroscopy.

TABLE 3

| Description | Peptide | Gene | Clone | SEQ ID NO |
|---|---|---|---|---|
| PDGF loop III in dendroaspin loop 2 | RKIEIVRKK | V1 | 26 | SEQ ID NO: 1 |
| PDGF loop I in dendroaspin loop 2 and *S pneumoniae* peptide in dendroapsin loop3 | ISRRLIDRTNANFL<br>FHLPYNHNWFAL | V2 | | SEQ ID NO: 22<br>SEQ ID NO: 23 |
| PDGF loop I in dendroaspin loop 2 | ISRRLIDRTNANFL | V3 | 41 | SEQ ID NO: 22 |

TABLE 3-continued

| Description | Peptide | Gene Clone | SEQ ID NO |
|---|---|---|---|
| PDGF loopI in dendroaspin loop 2 and CMV peptide in dendroaspin loop 3 | ISRRLIDRTNANFL<br>AGPPRYSRI | V4 | SEQ ID NO: 22<br>SEQ ID NO: 24 |
| Apo B 100 in dendroaspin loop 2 and S pneumoniae peptide in dendroaspin loop 3 | IEIGLEGKGFEPTLEALFGK<br>FHLPYNHNWFAL | V5 65 | SEQ ID NO: 25<br>SEQ ID NO: 23 |
| PDGF loop I in dendroaspin loop 2 and human HSP 60 peptide in dendroaspin loop 3 | ISRRLIDRTNANFL<br>AELKKQSKPVT | V6 72 | SEQ ID NO: 22<br>SEQ ID NO: 26 |
| PDGF loop III in dendroaspin loop 2 and S pneumoniae peptide in dendroaspin loop 3 | RKIEIVRKK<br>FHLPYNHNWFAL | V7 87 | SEQ ID NO: 1<br>SEQ ID NO: 23 |
| PDGF loop III in dendroaspin loop 2 and CMV peptide in dendroaspin loop 3 | RKIEIVRKK<br>AGPPRYSRI | V8 | SEQ ID NO: 1<br>SEQ ID NO: 24 |
| Human hsp60 B cell epitope type 1 in dendroaspin loop 3 | PGFGDNRKN | | SEQ ID NO: 28 |
| Human hsp60 B cell epitope type II in dendroaspin loop 3 | VQDVANNTNE | | SEQ ID NO: 29 |
| CMV pp65 91-100 in dendroaspin loop 3 | SVNVHNPTG | | SEQ ID NO: 30 |
| Partial CETP epitope in N-terminal and Porphyromonas gingivalis hsp epitope in aa 71-80 | MDFGFPEHLLVDFLQSLSGG<br>GGGRICYNHLGTKPPTTETC<br>QEDSCYKNIWTFDNIIRRGC<br>GCFTVQDVANNTNEYCCES<br>DKCNL | | SEQ ID NO: 31 |

3-b) Ability of Recombinant Immunogens to Compete with PDGF in Cell Migration Assay.

Cell Migration Inhibition Assay:

Cell migration inhibition assays were performed using Transwell Plates, 8 µm pore size and 6.5 mm insert diameter (Corning Life Sciences). Confluent cells were maintained in Serum Free DMEM media with 0.5% BSA for 24 hrs before the experiment. The plates were also coated with 100 µl of 100 µg/ml Invitrogen solution 24 hrs prior. Cells were harvested using trypsin and cell numbers determined before centrifuged and resuspended at a density of $1 \times 10^6$ cells/ml. Both chambers were then pre-incubated 30 min before addition of cells. A volume of 100 µl of cells were placed on the top chamber and the chemoattractant PDGF (with or without A15) added to the lower chamber. After an incubation period of 16 hrs at 37° C. and 5% $CO_2$, cells from the upper face of the membrane were removed and the migrated cells from the lower face fixed in methanol and stained using Diff-Quik solution. The membrane were then mounted on a microscopic slide and counted under 40× magnification in 5 random fields.

Results:

FIG. 2 shows the result of a cell migration inhibition assay expressed as a percentage of cells migrating as compared with PDGF alone at 20 ng ml$^{-1}$ (100%). Low values therefore indicate successful competitive inhibition of the effect of PDGF by recombinant proteins presenting PDGF receptor-binding domains (10 µM). A cyclic PDGF loop I peptide (called TROM), known to be effective, is compared at a higher concentration (200 µM).

3-c) PDGF-Like Proliferative Effects

Cell proliferation assay-MTT assay: The yellow tetrazolium MTT (3-(4,5-dimethylthiazolyl-2)-2,5-diphenyltetrazolium bromide) is reduced by metabolically active cells, in part by the action of dehydrogenase enzymes, to generate reducing equivalents such as NADH and NADPH. The resulting intracellular purple formazan can be solubilized and quantified by spectrophotometric means. This protocol, although a manual to a MTT assay kit, can be followed for general use. MTT stock solution: 5 mg/ml MTT (Promega) in RPMI-1640 without phenol red. This solution is filtered through a 0.2 mm filter and stored at 2-8° C. MTT working solution: 1:10 dilution of the 5 mg/ml stock (MTT in RPMI without phenol red). 1. Wash cultured cells with warm RPMI-1640 without phenol red. 2. Prepare MTT working solution. 3. Add MTT working solution into wells being assayed, for example 1.0 ml for each well of 12-well plate. Incubate at 37° C. for 30 min to 3 hrs (this time depends on cell density and cell type). 4. At the end of the incubation period, the medium can be moved if working with attached cells. 5. The converted dye is solubilized with 1 ml acidic isopropanol (0.04 M HCl in absolute isopropanol). Pipette up and down several times to make sure the converted dye dissolves completely. 6. Transfer the dye solution with the cells into a 1.5 ml eppendorf tube and centrifuge at 13,000 rpm for 2 min. 7. Transfer the supernatant into a new eppendorf tube. Absorbance of the converted dye is measured at a wavelength of 570 nm with background subtraction at 650 nm. For the measurement, use Spectrophotometer and disposable plastic cuvettes.

Results:

FIG. 3 compares the inhibitory effect on PDGF-induced proliferation of 5 immunogen constructs as compared with cPDGF. High values indicate maximum competitive inhibition.

3-d) Immunoreactivity of Constructs

Antibody and Antigen Titre Assay:

We use antibody and antigen ELISA-based assay for characterization of recombinant proteins (antigens). In order to perform ELISA assay. GST-proteins were dialyzed to get rid off Tris and NaCl after affinity column. GST-protein cannot be freeze-dried as it contain high salts (NaCl). The ELISA assay includes 1. Adsorb predetermined maximal concentration of antigen to microtitre plate. Dilute in coating buffer and incubate 100 μl per well overnight at 4° C. 2. Aspirate antigen solution and block unbound sites on the plastic by incubating 100 μl of blocking solution per well for 15 min. 3. Wash off unbound antigen and block protein three times with wash buffer. Add 100-fold dilutions of antibody across the plate. 4. Wash off unbound antibody three times with wash buffer. 5. Add HRP-conjugated second antibody at the recommended or predetermined dilution. Incubate 100 μl per well for one hour at ambient temperature. 6. Wash off unbound label three times with wash buffer. 7. Add enzyme and substrate. Incubate 100 μA per well at ambient temperature until colour develops sufficiently (ideal approx. 30 min). 8. Do not wash off. Add 50 μA of the appropriate stopping solution and assess either visually or quantitatively in a spectrophotometer designed to read microtitre plates.

Results:

FIG. 4 A shows the saturable reactivity of PDGF loop I constructs (constructs V2, V3, V4 and V6 as disclosed in table 3) with anti-PDGF BB polyclonal antibody. V1, a PDGF loop III construct, is unreactive.

FIG. 4B shows a similar assay using an anti-Streptococcal polyclonal antibody (produced by *Streptococca pneumoniae* vaccine). Constructs V2 and V7, carrying the Streptococcal determinant, are reactive, V1 is a negative control.

4) Generation of Multispecific Vaccines 4-a) Selection of Epitopes

A series of epitopes were derived from atherosclerotic protein antigens (oxLDL and HSP) and atherosclerotic pathogens (HCMV), Cpn and *p. gingivalis*). Examples of the epitopes are given in table 4. The epitopes were prepared as outlined in section 1-b above.

TABLE 4

Peptides used in the development of multispecific vaccines

| Peptide origin | Peptide sequence | SEQ ID No |
|---|---|---|
| CMV pp65 | NLVPMVATV | 27 |
| CMV PP65 | SVNVHNPTG | 30 |
| CETP | MDFGFPEHLLVDFLQSLS | 32 |

TABLE 4-continued

Peptides used in the development of multispecific vaccines

| Peptide origin | Peptide sequence | SEQ ID No |
|---|---|---|
| Human hsp60 B cell epitope type 1 | PGFGDNRKNQ | 34 |
| *P. gingivalis* | VKEVASKTND | 35 |
| MicroHSP | EGEALSTLVVNKIRGT | 36 |
| Cpn1 | DYVFDRI | 37 |
| Cpn2 | QAVANGGAI | 38 |
| ApoB1 | IEIGLEGKGFEPTLEALFGK | 25 |
| ApoB2 | KTTKQSFDLSVKAQY | 39 |
| CETP | RDGFLLLQMDFGFPEHLLVDFLQSLS | 40 |
| *S pneumoniae* | FHLPYNHNWFAL | 23 |
| CMV pp65 | AGPPRYSRI | 24 |
| *Porphyromonas gingivalis* hsp | CFTVQDVANNTNEYC | 32 |
| Partial CETP epitope in N-terminal and *Porphyromonas gingivalis* hsp epitope in aa 71-80 | MDFGFPEHLLVDFLQSLSGGGGGRICYNHLGTKPPTTETCQEDSCYKNIWTFDNIIRRGCGCFTVQDVANNTNEYCCESDKCNL | 31 |
| *M bovis* hsp60 | AELKKQSKPVT | 26 |
| Human hsp60 | PGFGDNRKN | 28 |
| Human hsp60 | VQDVANNTNE | 29 |

4-b) Preparation of Multispecific Vaccines

Examples of epitope combinations tested are provided in table 5.

TABLE 5

| Epitope combinations |
|---|
| ApoB1 + CMV |
| ApoB1 + CMV + cpn 1 |
| ApoB1 + CMV + cpn 2 |
| ApoB1 + CMV + cpn (1 + 2) |
| ApoB1 + CMV + cpn (2 + 1) |
| ApoB2 + CMV + cpn 1 |
| ApoB2 + CMV + cpn 2 |
| ApoB2 + CMV + cpn (1 + 2) |
| ApoB2 + CMV + cpn (2 + 1) |
| ApoB1 + hHSP |
| ApoB1 + hHSP |
| ApoB1 + hHSP + cpn 1 |
| ApoB1 + hHSP + cpn 2 |
| ApoB1 + hHSP + cpn (1 + 2) |
| ApoB1 + hHSP + cpn (2 + 1) |
| ApoB2 + hHSP + cpn 1 |
| ApoB2 + hHSP + cpn 2 |
| ApoB2 + hHSP + cpn (1 + 2) |
| ApoB2 + hHSP + cpn (2 + 1) |
| Glutathione transferase (GST) |
| (hHSP60, B-cell type1)in dendoaspin loop III |
| (hHSP60, B-cell typeII)in dendoaspin loop III |
| CETP + *P. gingivalis* (*Porphyromonas gingivalis*) |
| microHSP65 + CMV |
| microHSP65 + hHSP60 |

A number of recombinant immunogens comprising a carrier protein with the aforementioned epitope combinations were generated by incorporating the epitope combinations into a carrier protein. The epitope combinations were linked to either N-terminus or C-terminus, or grafted into either loops 2 and/or 3 of a dendroaspin scaffold (as described in section 3-a above, Lu et al., Thromb Haemost. 2006, 96, 642-651) or conjugate to Keyhole limpet hemocyanin (KLH) from Megathura crenulata (for the peptides and small recombinant molecules) via Cys residues normally located at the N-terminus. The gene of each recombinant immunogen was synthesized using both forward and reverse primers containing the gene codes encoding peptide epitopes using one or more than one-run PCRs to produce a complete gene sequence. If GST-linked recombinant molecules were used, these molecules were purified by ion-exchange column (DE52, an anion exchange resin), eluted with 100 mM NaCl, 50 mM tris-HCl, pH 7.25 at 4° C., and dialyzed at 4° C. to get rid of salt. Recombinant molecules without GST were purified as described in section 3-a) above. KLH was used for conjugation of small peptide epitopes.

5) Activity of Multispecific Vaccines 5-a) Immune Response in an Animal Model

The ability of the recombinant immunogens to generate an immune response in BALB/C mice models, C57/BL6 mice models and Apob$^{tm2Sgy}$ Ldlr$^{tm1Her/J}$ KO-mice models. Mice were immunized using a repetitive, multiple site immunization strategy (RIMMS). Groups of 10 of 6-8-week-old BALB/c mice were inoculated with 4 µg of recombinant immunogen mixed with Freund's adjuvant 5 times respectively. The immunization was carried out subcutaneously on 8 sites on days 0, 2, 5, 7 and 9. On day 12 and 21 blood sample will be collected to test the antibody response. Recombinant molecules were first tested in Balb/C or C57/BL6 mice to observe immune responses, then, based on their immune reposes, the molecules were further tested in KO mice to investigate the effect of these peptides on atherosclerosis.

Serum samples of immunized and naïve mice were tested for IgG antibodies using OD values at a dilution of 1:100 (or 200) on ELISA plates coated with antigens. Cut-off value for positivity was calculated as mean OD of naïve mouse sera+ 3×SD. Serum samples showing higher OD on antigen than on control antigen are considered positive, the other is determined by the highest dilution of serum giving an OD reading (at 450 nm)≧1. In this regard, titre can be assessed as non-immunoreactivity (<200), low immunoreactivity (200≦titre<800), good immunoreactivity (800≦titre<3200) and very good immunoreactivity ((titre 3200)

The results of the RIMMS are illustrated in table 6 below.

TABLE 6

| Epitopes | Carrier | Immune response On BALB/C or C57/BL6 | Immune response on KO- mouse model |
|---|---|---|---|
| ApoB1 + CMV | GST-dendroaspin | Good | |
| ApoB1 + hHSP | KLH | | Very Good |
| ApoB1 + hHSP | GST-dendroaspin | Very Good | |
| ApoB1 + hHSP + cpn (1 + 2) | GST-dendroaspin | Very Good | |
| (hHSP60, B-cell type1)in dendoaspin loop III | GST-dendroaspin | Good | |
| (hHSP60, B-cell typeII)in dendoaspin loop III | GST-dendroaspin | Good | |

TABLE 6-continued

| Epitopes | Carrier | Immune response On BALB/C or C57/BL6 | Immune response on KO- mouse model |
|---|---|---|---|
| CETP + P. gingivalis (Porphyromonas gingivalis) | GST-dendroaspin | Very Good | |
| microHSP65 + CMV | GST-dendroaspin | Good | |
| microHSP65 + hHSP60 | GST-dendroaspin | Good | |

5-b) Activity of ApoB and Hhsp60 Bi-Specific Vaccine

LDL receptor-deficient mice expressing ApoB-100 were immunized with a combination of two peptides derived from ApoB1 (IEIGLEGKGFEPTLEALFGK, SEQ ID NO:25) and hHSP60 (AELKKQSKPVT, SEQ ID NO:26). Immunization with a bispecific recombinant immunogen was shown to provide a synergistic protection from progression of atherosclerotic lesion.

5-c) Immune Response

Apob$^{tm2Sgy}$Ldlr$^{tm1Her/J}$ mice were immunized with combinations of ApoB and hHSP epitopes conjugated to keyhole limpet hemocyanin (KLH) as a carrier protein. The peptides were given either in combination, as a bi-specific immunogen, or in a single form, together with complete/incomplete Freund's adjuvant. Mice were fed with high-fat diet for 7 weeks then sacrificed. Peptide-specific antibody responses were detected in the sera by ELISA. As illustrated in table 7 below, he antibody levels induced by the immunization with a combination of both peptides showed OD values similar to that of obtained by immunization with either the ApoB or the hHSP peptide.

TABLE 7

| Proteins used for immunization | No of mouse | ELISA antigens | |
|---|---|---|---|
| | | ApoB1 peptide OD at 1:100 serum dilution Week 8 | hHSP60 peptide Week 8 |
| ApoB1-KLH | 1. ♂ | 1.329 | 0.542 |
| | 2. ♂ | 1.236 | 0.289 |
| | 3. ♀ | 1.152 | 0.823 |
| | 4. ♀ | 1.194 | 0.402 |
| | 5. ♀ | 1.21 | 0.574 |
| Mean | | 1.224 | 0.526 |
| ApoB1 + hHSP60-KLH | 1. ♂ | 1.227 | 1.368 |
| | 2. ♂ | 1.546 | 1.405 |
| | 3. ♂ | 1.449 | 1.556 |
| | 4. ♀ | 1.437 | 1.282 |
| | 5. ♀ | 1.142 | 1.215 |
| | 6. ♀ | 1.229 | 1.338 |
| | 7. ♀ | 1.303 | 1.396 |
| Mean | | 1.333 | 1.366 |
| hHSP60-KLH | 1. ♂ | 0.918 | 1.337 |
| | 2. ♂ | 0.718 | 1.482 |
| | 3. ♂ | 1.304 | 1.306 |
| | 4. ♂ | 1.259 | 1.318 |
| | 5. ♀ | 0.323 | 1.461 |
| | 6. ♀ | 1.428 | 1.149 |
| | 7. ♀ | 0.682 | 1.192 |
| | 8. ♀ | 0.85 | 1.199 |
| Mean | | 0.935 | 1.306 |
| KLH | 1. ♂ | 0.221 | 0.025 |
| | 2. ♂ | 0.163 | 0.018 |
| | 3. ♀ | 0.355 | 0.031 |
| | 4. ♀ | 0.301 | 0.019 |
| Mean | | 0.260 | 0.023 |

5-d) Anti-Atherosclerotic Effect

Aortic tissues were histologically analyzed, as illustrated in FIG. 5A-D. Results: Histological analysis demonstrated that atherosclerotic lesions in the aortic sinus were 41.34% smaller in size in mice immunized with the combination of the two peptides (FIG. 5D) than in the control mice (FIG. 5A). The lesions were 14.66% smaller following immunization with ApoB1 peptide alone (FIG. 5B), and 21.15% smaller after immunization with hHSP60 peptide alone (FIG. 5C) than in control mice.

These results demonstrate that combination of ApoB1 and hHSP peptide antigens in a bi-specific immunogen engenders a synergistic effect and can reduce atherosclerotic lesions in this mouse model.

5-e) Macrophage Levels

Infiltration of macrophages into atherosclerotic lesions in the $Apob^{tm2Sgy}Ldlr^{tm1Her/J}$ mice were quantified by staining with anti-CD68. Sections of the tissue sample (5 μm thick) were stained with hematoxylin-eosin (H.E.) and examined under a light microscope. Macrophage levels were compared in a sample obtained from mice immunized with adjuvant only (control), mice immunized with ApoB only, mice immunized with hHSP60 only and mice immunized with the bi-specific ApoB1+hHSP60 immunogen.

The relative numbers of macrophages found in atherosclerotic lesions form each mouse group is illustrated in FIG. 6. The results of the histoimmunological analysis demonstrate that the number of macrophages (CD68+ cells) found within lesions of atherosclerosis are fewer in mice immunized with a bi-specific immunogen of HSP60 and apoB1, than the number of macrophages seen in either mice immunized with either HSP60 or apoB1 alone. This indicated that animals immunized with the bi-specific immunogen have less formation of atherosclerotic lesions than mice immunized with either HSP60 or apoB1 alone.

5-f) Activity of ApoB1, Hhsp60, cpn 1 and cpn 2 Tetra-Specific Vaccine

BALB/c mice (female, 6 weeks of age) were immunized with a tetra-specific GST linked immunogen comprising ApoB1 peptide1, hHSP60, cpn 1 and cpn 2 in dendroaspin scaffold.

A nucleic acid construct encoding the tetra-specific immunogen was synthesized by PCR and cloned into PGEX-3X vector. The protein was expressed in E. coli. as a GST-fusion protein and purified by affinity and ion exchange columns.

The GST-tetra-specific immunogen, in combination with Freund's adjuvant, was used for immunization of BALB/C mice. Peptide-specific antibody levels were demonstrated by ELISA, the results of which are indicated in table 8 below.

TABLE 8

| antigen | ApoB peptide | | | hHSP60 peptide | | | C. pn. peptide | | |
|---|---|---|---|---|---|---|---|---|---|
| No of mice | 191 | GST-dendroasp | GST | 191 | GST-dendroasp | GST | 191 | GST-dendroasp | GST |
| | 1.252 | 0.018 | 0.029 | 0.051 | 0.009 | 0.010 | 1.256 | 0.03 | 0.034 |
| | 1.307 | 0.027 | 0.022 | 0.360 | 0.008 | 0.011 | 1.577 | 0.027 | 0.074 |
| | 1.442 | 0.029 | 0.025 | 0.010 | 0.009 | 0.010 | 1.256 | 0.016 | 0.082 |
| | 1.268 | 0.035 | 0.018 | 0.062 | 0.010 | 0.018 | 1.384 | 0.035 | 0.068 |
| | 1.059 | 0.031 | | 0.286 | 0.020 | 0.009 | 0.585 | 0.041 | 0.176 |
| | 1.34 | 0.036 | 0.021 | 0.526 | 0.008 | 0.008 | | 0.035 | 0.08 |
| | 1.593 | 0.023 | 0.019 | 0.009 | 0.009 | 0.009 | 1.314 | 0.025 | 0.077 |
| | 1.623 | 0.033 | 0.053 | 0.172 | 0.010 | 0.009 | 0.534 | 0.025 | 0.104 |
| | 1.057 | 0.063 | 0.051 | 0.076 | 0.010 | 0.009 | 0.254 | 0.037 | 0.112 |
| | 1.245 | 0.067 | 0.014 | 0.125 | 0.009 | 0.010 | 1.369 | 0.012 | 0.137 |
| Mean | 1.319 | 0.036 | 0.028 | 0.168 | 0.010 | 0.010 | 1.059 | 0.028 | 0.094 |

High levels of ApoB-specific and Cpn-specific antibody responses were detected an all immunized mice, while the hHSP60-specific antibody responses were somewhat lower. These findings show that the tetra-specific immunogen has the multiple antigenic activities and specificity, which could be used for the development of a multivalent vaccine against atherosclerosis.

5-g) Activity of CETP+p.gingivalis Bi-Specific Vaccine

BALB/c mice (female, 6 weeks of age) were immunized with a bi-specific GST linked recombinant immunogen comprising CETP peptide+a selected epitope from p.gingivalis in dendroaspin scaffold.

A nucleic acid construct encoding the bi-specific immunogen was synthesized by PCR and cloned into PGEX-3X vector. The protein was expressed in E. coli. as a GST-fusion protein and purified by affinity and ion exchange columns. The GST-bi-specific immunogen, in combination with Freund's adjuvant, was used for immunization of BALB/C mice.

BALB/c mice were immunized with 4 μg of the bi-specific immunogen 5 times each. The immunization was carried out subcutaneously into 8 sites on days 0, 2, 5, 7 and 9. Groups of 7 mice received the protein mixed with Freund's adjuvant. On day 12 and 21 two mice from each immunization group respectively were euthanized for blood collection and their spleen was homogenized and cryo-preserved for further tests.

The tables show the OD values of the samples of individual mice measured on different ELISA antigens. Peptide-specific antibody levels were demonstrated by ELISA, the results of which are indicated in table 9 below. OD values over Cut off value of OD 0,100 are shown in bold.

TABLE 9

| | Bi-specific immunogen Freund's | | | | | | | | |
|---|---|---|---|---|---|---|---|---|---|
| Immu-niza- | hHSP60, B-cell type1 | | | hHSP60, B-cell typeII | | | P. gingivalis | | |
| tion | 0 | 12 | 21 | 0 | 12 | 21 | 0 | 12 | 21 |
| 1 | 0.024 | 1.140 | | 0.020 | 1.049 | | 0.031 | 1.577 | |
| 2 | 0.022 | 0.472 | | 0.021 | 0.465 | | 0.033 | 1.166 | |
| 3 | 0.020 | | 0.124 | 0.025 | | 0.054 | 0.025 | | 1.452 |
| 4 | 0.022 | | 0.932 | 0.023 | | 0.912 | 0.028 | | 1.384 |
| 5 | | | 1.055 | | | 1.055 | | | 2.158 |
| 6 | | | 0.949 | | | 0.786 | | | 1.843 |

These results demonstrate that a bispecific immunogen against *P. gingivalis* is also able to generate an immune response against the homologous hHSP60, B-cell type1 and hHSP60, B-cell typeII polypeptides.

6) Development of the Vaccine 6-a) Summary of Approach

The broad features of the development of the vaccine are as follows. Mice are immunised with the antigen and the antibody raised purified over an affinity column. The sequence within the variable region responsible for binding is identified either by sequencing mRNA isolated from hybridomas or of the variable region of the isolated antibody. These sequences are incorporated into a recombinant antibody expression system. The ability of the antibody to block atherosclerosis is tested in an animal model. BalbC mice are immunised with a selection of HSP60 peptides (linear or cyclic). Peptides engendering the highest inhibitory titre are then used to immunise mice. If necessary, a recombinant antibody library is also used at this stage. As before, the primary sequence responsible for the affinity of the antibody is used in development of a DNA vaccine. The bi-specific vaccine is developed from a combination of both the above.

6-b-i) Fab/scFv production. Fusion is be used for the production of single chain variable fragments (scFv) and Fab recombinant antibodies, which are used to generate bispecific molecules. ScFvs offer several advantages over monoclonal antibodies such as low kidney uptake, rapid blood clearance, and a lower negative response by the human immune system due to their small size.

6-b-ii) Construction of an scFv from monoclonal cell lines. This includes isolation of mRNA from hybridomas expressing antibody as of high affinity and selectivity. Isolation of mRNA is performed in a single tube by hybridising the polyadenylated RNA directly from tissue lysates to oligo(dT)$_{25}$-bound magnetic particles. Either MPG® Direct mRNA Purification Kit (MDRK1010) or MPG® Guanidine Direct mRNA Purification Kit (MGRK1010) are used following the manufacture's instruction. The isolated mRNA is then analysed for yield, purity and integrity by spectrophotometry, gel electrophoresis and ultimately solution phase RT-PCR. The mRNA from the monoclonal is cloned to create a cDNA vector from which the variable heavy (Vh) and light (Vl) chains are then subcloned into an expression vector.

6-b-iii) Construction of an scFv from antibody libraries made available by the scientific community. Certain libraries have been made available by the scientific community and these are used according to the procedures described above. The library is screened and following the identification of a highly specific monoclonal antibody, the hybridoma cell line producing the antibody is used as a source of Vl and Vh fragments. Hybridoma mRNA is isolated from the cells using above standard methods and a cDNA copy prepared using the reverse transcription (RT) PCR with random oligonucleotide primers.

6-b-iv) Reverse transcription-PCR(RT-PCR) and in vitro transcription. Reverse transcription is performed using Superscript reverse transcriptase (GIBCO/BRL) according to the supplier's instructions. PCR is be performed using Taq DNA polymerase (GIBCO/BRL) in the presence of 5% (vol/vol) dimethyl sulfoxide (4 min at 94° C., followed by 3 cycles of 30 sec at 94° C., 30 sec at 37° C., and 2 min at 72° C., followed by 10 similar cycles at 60° C., 20 similar cycles at 60° C. instead of 37° C. with elongation at 72° C. prolonged by 15 sec per cycle and finished by 10 min at 72° C.).

6-b-v) In vitro coupled transcription-translation. After the fifth round of ribosome display, PCR products are cloned into the suitable vector (such as pTFT74). In vitro coupled transcription-translation in the S-30 *E. coli* system is performed using 50 µg/ml plasmid DNA and conditions similar to those described above with the following modifications. A coupled transcription-translation is carried out for 30 min at 37° C., and the reaction mixture supplemented with T7 RNA polymerase at 2000 Units/ml and 0.5 mM UTP and TTP. The mixture contained [$^{35}$S]methionine at 50 αCi/ml (1 αCi=37 kBq) and each amino acid except methionine at 0.35 mM. After translation, the reaction mixture is diluted 4-fold with PBS and bound to immobilized antigen peptide in a microtiter well. After 60 min of incubation with gentle shaking, microtiter wells are washed five times with PBS containing 0.1% Tween 20, and bound radioactive protein eluted with 0.1 M triethylamine. Eluted protein (antibody) is be quantified in a scintillation counter.

6-b-vi) Antibody expression. For large scale protein expression, selected antibody sequences are cloned in either pGEX-3X or pET32b vectors and transformed into *E. coli*. Expression and purification of GST fusion proteins is performed according to standard methods. Antibodies are also cloned into a eukaryotic cell expression vector and expressed in eukaryotic cells such as yeast.

6-c-i) Production of CDR libraries by phage display. Phage display is the process by which the phage is made to 'display' human antibody proteins on its surface. Genes from the human antibody gene libraries are inserted into a population of phage. Each phage carries the genes for a different antibody and thus displays a different antibody on its surface. These genes can be recovered and made available for use in the onward development and potential manufacture of an antibody therapeutic product.

6-c-ii) Production of epitopes by ribosome display system. With "ribosome display", a novel method has been developed in which whole functional proteins can now be enriched in a cell-free system for their binding function, without the use of any cells, vectors, phages or transformation. This technology is based on in vitro translation, in which both the mRNA and the protein product do not leave the ribosome. This technology includes construction of ribosome display library, in Vitro translation of scFv a single chain fragment of antibody library, affinity selection of ribosome complexes and RNA isolation, ELISA of single chain fragment of antibody, PCR analysis of the library for the presence of corrected mutants, protein expression, antigen affinity chromatography, western blots, determination of the antigen dissociation constant in solution by competition BIAcore, etc.

6-d-i) DNA vaccination. DNA vaccination is used to express the selected epitopes or the appropriate antibody (including the bifunctional antibody). Experimentally, this will be carried out using a mammalian cell transfection kit protocol (www.SpecialtyMedia.com). The pcDNA (Invitrogen) vectors encoding human HSP65 or mycobacterial HSP65 and PDGF are constructed and used for expression of antigen and DNA vaccination. Transfection will be carried out by the calcium phosphate-mediated method involves mixing DNA directly with CaCl2 and a phosphate buffer to form a fine precipitate, which is dispersed over the cultured cells. The calcium phosphate transfection protocol is routinely used for both transient and stable transfection of a variety of cell types.

6-d-ii) DNA vaccination. Gene gun bombardment or intramuscular (i.m.) injection of naked DNA protocol are used for intramuscular immunisation.

7) Testing of Antibodies 7-a) ELISA: The tracking and quantification of the properties of each antibody are checked against each antigen using standard ELISA techniques.

7-b) Determination of the antigen dissociation constant in solution by competition. BIAcore analysis is performed under mass-transport by using a sensor chip CM5 (Pharmacia) coated with 15,000 resonance units of BSA-antigen conjugate or with only BSA as a control. Each binding-regeneration cycle will be performed with a constant flow rate of 25 µl/min by using HBST (20 mM Hepes, pH 7.2/150 mM NaCl/0.005% Tween 20). Samples of 250 µl of antibody in HBST, containing various amounts of antigen, will be injected by means of the sample loop of the system, followed by regeneration of the surface by injection of 20 µl of 6 M guanidinium chloride in HBST. Inhibition studies are carried out by coincubation of antibodies with antigen peptide at a series of concentrations for at least 1 hour at 4° C. before injection. Data are evaluated by using BIAEVALUATION software (Pharmacia) and KALEIDAGRAPH (Synergy Software, Reading, Pa.). Slopes of the association phase of linear sensograms is plotted against the corresponding total antigen concentrations.

7-c) Determination of the ability of antibodies to inhibit atherosclerotic lesion formation. 10 week old, male LDL receptor (LDLR)-deficient mice on normal chow are immunised with an appropriate amount of the heat shock protein-PDGF peptide complex (as determined from the immunogenicity experiments described in the previous section) The response of these animals is compared to animals immunised with peptide alone, HSP alone or buffer alone. A second immunisation will be carried out after 1 week. The animals are then be separated into two groups, one receiving normal chow and the other a high-cholesterol diet (1.25% cholesterol, 0% cholate; Research Diets). After 14 weeks, mice are killed, blood taken, and aortas removed and perfused with 0.9% NaCl. Aortas are dissected into 3 parts—the roots and arches are snap-frozen in Tissue-Tek® OCT Compound for cryostat sectioning and the abdominal parts fixed in 2% paraformaldehyde. The extent of atherosclerosis is assessed in aortic roots and thoraco-abdominal aortas according to standardised methods in which quantification is performed by computer image analysis (Zeiss software). This involves calculation of the average area of lesion in 6 sections 50 µm distant from each other in the aorta root; dividing this area of lipid deposition (stained with Sudan IV) by the total valve surface. The thoraco-abdominal aorta is examined by a longitudinal incision along the ventral midline, staining the lesion areas in an en face preparation with Sudan IV. The percentage of lipid deposition is calculated by dividing the Sudan IV-stained area by the total thoraco-abdominal surface.

Data sets containing multiple groups are analyzed by ANOVA. Mean values between 2 groups are compared by a 2-tailed Student's t test, after an F test for homogeneity of variances had been performed. If data fail to meet the requirements for use of the parametric t test, a Mann-Whitney U test is used. Differences are considered statistically significant at a value of $P<0.05$.

8) Identification of Specific Hsp-Peptide Complexes Produced by Foam Cells Used to Generate Bifunctional Vaccines which are Capable of Targeting Foam Cells 8-a) In vitro foam cell model. This is based upon the method of Kellner-Weibel eta/using lipid loaded phorbol ester differentiated THP-1 macrophages (0.1 µM/24 h) as well as the J774 mouse macrophage cell line (Kellner-Weibel et al, Arterioscler Thromb Vasc Biol 1998, 18, 423-431). Human LDL is fractionated from plasma by centrifugation and acetylated by the method of Basu et al (Basu et al, Proc Natl Acad Sci USA 1976, 73, 3178-3182). In some experiments, the monocyte fraction is isolated from freshly drawn blood using density gradient to prepare mononuclear leukocytes from which the monocytes are separated by negative depletion of lymphocytes using magnetic beads. Cells are cultured in the presence of acyl-coenzyme A: cholesterol acyltransferase inhibitor (ACAT inhibitor, 58035), which produces a rapid accumulation of free cholesterol in the cell.

8-b) Preparation of purified HSP from foam cells. Cells are lysed by sonication in buffer ($10^9$ cells per 100 ml of lysis buffer) containing 20 mM Tris-HCl (pH 7.9), 0.5 M NaCl, 5 mM imidazole, 0.1% Nonidet P-40 and protease inhibitors followed by incubation for 0 min on ice. The lysate is centrifuged at 10000×g for 1 h and the supernatant from this step subjected to further centrifugation at 100000 g (Beckman Ti75 rotor for 2 h. The purification of individual HSP is then be carried out as described above (Purified heat shock proteins).

8-c) Identification of foam cell specific peptides associated with heat shock proteins. The purified HSPs are washed during purification to remove any loosely attached peptides. Attached peptide is then be eluted from the protein with trifluoroacetic acid and analysed using surface enhanced laser desorption/ionisation (SELDI) mass spectrometry. (Ciphergen Biomarker System). The peptide fraction is analysed on each of the chip types that are available (binding through positive or negative charge, hydrophobicity and metal chelation.). Those peptides that show enhanced levels compared to cells which are not in the foam cell phenotype are selected for complete identification of primary structure by matrix-assisted laser. This is an approach that is applicable to individual lesions since HSP/antigenic peptides can be isolated from resected tumour tissue and used for immunisation (autologous immunisation).

8-d) Preparation of HSP-foam cell specific peptide complexes as vaccine against atherosclerosis. HSPs are be complexed to each of the peptides identified as specific for foam cells according to the procedures described for the PDGF peptides in section (Enzyme-linked immunosorbent spot assay). The ability of these complexes to act as vaccines against foam cells, either blocking their formation or reversing established fatty streaks are also be determined in a similar manner as described above (determination of the immunogenicity of heat shock protein-PDGF complexes).

8-e) Production of a DNA vaccine based upon a chimerical fusion gene incorporating HSP and a peptide antigen specific for the neutralisation of PDGF or foam cells. The translation of DNA vaccines into clinical settings has been hampered by their limited potency. This arises because after intramuscular or intradermal injection of the plasmid DNA, myocytes and keratinocytes are predominantly transfected. These cells lack the ability to generate a strong primary immune response. One way which has been proposed to overcome this drawback is to target bone marrow derived antigen presenting cells, especially dendritic cells (Hauser et al, Gene Ther 2004, 11, 924-932; Liao et al, Mol Ther 2004; 9:757-64). This has recently been shown to be possible by preparing a chimeric fusion gene between the antigen and a HSP. By this approach, it was possible to generate a strong T-cell and B-cell response.

Alternatively a so-called troybody construct encoding a specific anti-Hsp antibody that also carries one or more PDGF or foam cell antigen epitope within its structure may be used (Lauvrak et al, Biochem Soc Trans 2002, 30: 500-506).

9) Oral Vaccine

Microsomes from antigen presenting cells (APCs) such as macrophages consist of cell free membrane vesicles of the endoplasmic reticulum (ER), the cellular compartment where processed antigenic peptides are complexed with MHC and interact with other factors for eventual presentation on the surface of APCs. Once on the surface they are able to interact with, and stimulate, T cells. A particular benefit of the technology is that the ER is efficiently loaded in vitro with known 'protective' peptides, resulting in microsomes that have a high level of correctly assembled MHC-peptide complexes presented in the membrane, mimicking the APC. The microsomes can be injected into recipients where they directly interact with and stimulate T cells.

It is particularly useful to generate inverted or 'inside-out' microsomes in which membrane-bound MHC-peptide complexes are presented on the external surface of the microsomes, rather than being oriented towards the lumen as is the case with standard preparations. The use of repeated freeze-thaw treatment of microsomal preparations to produce such inverted microsomes is well-known in the art and is briefly summarised below.

9-a) Purification of PBMC from Buffy Coat

Peripheral blood mononuclear cells (PBMCs) are prepared from fresh buffy coats of healthy blood donors by Ficoll density centrifugation (Ficoll-Paque, Pharmacia, Uppsala, Sweden). Buffy coats were diluted 1:2 in 0.9% NaCl, and 35 ml were layered onto 15 ml of Ficoll Paque and centrifuged for 25 min at 400 g. Cells were washed twice in RPMI 1640 (Gibco, Grand Island, N.Y.). For some experiments PBMC were depleted of adherent cells by a 2-h incubation at 37° C.

9-b) Purification of Dendritic Cells

To prepare dendritic cells (DCs) the PBMCs are transferred into a large cell culture flask and incubated at 37° C. in a humidified cell culture incubator for 1 hr and in 50 ml RPMI medium/3%/human serum. After 1 hour, cells in suspension are collected as a lymphocyte fraction, while the adhered fraction is monocyte enriched.

To achieve differentiation of monocytes into DC, fresh RPMI media/3% human sera with antibiotics and supplemented with 8001 U/ml GM-CSF and 10001 U/ml IL-4 is added to the monocytes, after 3 days the media is replaced with fresh media containing 16001 U/ml GM-CSF and 10001 U/ml IL-4.

On day 6, both antigen (peptide or protein) and 10 ng/ml TNF-α are added to achieve antigen presentation and DC maturation respectively. On day 9, the matured and loaded DCs are used for subsequent T cell stimulation reactions.

9-c) T Cell Preparation

The lymphocyte population is enriched for the CD4+ cells by an anti-CD4-MACS® magnetic bead column. MACS MicroBeads are superparamagnetic particles of approximately 50 nanometers in diameter. They are composed of a biodegradable matrix, and it is therefore not necessary to remove them from cells after the separation process. The purified CD4+ T cells are sustained in culture with 20-50 IU/ml recombinant human IL-2 or frozen until further use. The matured and loaded DC are incubated with mitomycin C before co-culturing with the autologous CD4+ T cells at a ratio of T:DC of 10:1 and incubated for 24 hrs—4 days after which the cells mediated response is measured by cytokine profile analysis for IFN-γ (Th1) and IL-4 (Th2) measured by intracellular staining or by Elispot. T cell proliferation is measured by CFSE labelling, BrdU treatment or thymidine incorporation assay.

9-d) Testing Immunogenicity

On day 9 of DC culture, the loaded DC groups (DC incubated with 20 ug/ml mitomycin C before incubation with T cells) are divided into 2 further groups, for use as loaded live DC or as loaded DC sonicates (microsomes and plasma membrane).

The following groups of DC are incubated with T cell in triplicate wells of 96 well plates:
1. Unloaded mature DC:T cell
2. Loaded mature DC:T cell
3. Unloaded DC sonicates:T cell
4. Loaded DC sonicates:T cell
5. T cells as negative control
6. T cells incubated with a PHA as a positive control
7. PBS $1 \times 10^5$ lymphocytes are cocultured with the following concentrations of DC; $1 \times 10^4$, $5 \times 10^3$ and $5 \times 10^3$ and with the following concentrations of sonicates; 1 ul of OD 60, 2.5 ul of OD 60, and 4 ul of OD 60. After 24-48 hour incubation coculture, the supernatant is collected for cytokine ELISA measurement for IL-2 (measure of T-cell activation), IFN-γ (Th1 response), and IL-4 (Th2 response).

To measure T cell proliferation. lymphocytes are labelled with CFSE (Cell Trace CFSE kit, Molecular Probes) before incubation with the DC and sonicates. For a negative control, lymphocytes are incubated with phytohaemoglutinin (PHA). Cells are taken for FACS analysis after 3-5 days of culture with DC or sonicates.

9-e) Purification of Sonicates from DC

The following procedure is used for sonicate preparation
1. Resuspend cells ($2 \times 10^8$/ml) in $H_2O$ plus PMSF (1 mM)
2. Homogenise in fine Dounce for 20 to 40 strokes
Add ($10^8$ cells/ml) STKMM buffer (250 mM sucrose, 50 mM triethanolamine=HCl pH 7.5, 50 mM KAc, 5 mM $MgAc_2$, 0.1% β-mercaptoethanol. Add PMSF just before to a final concentration of 10 μg/ml), and mixing well
4. Spin at 75000 rpm (10000 g) for 10 min at 4° C. in JK-18 tube to remove the nuclear fraction
5. Collect supernatant to a new tube, sonicate and spin at 100000 g for 60 mins at 4° C.
6. Carefully washing the pellets (containing ER, plasma membrane) with STKMM buffer
Homogenise and resuspend pellet in (200 ul/$10^8$ cells) RM buffer (50 mM HEPES, pH 7.2, 250 mM sucrose, 50 mM potassium acetate, 2 mM magnesium acetate)
8. Check OD at 280 nm and make up a final concentration of OD 60
9. Snap freeze aliquoted tubes in liquid nitrogen
10. Store sonicates in either liquid nitrogen or −80° C.

9-f) Microsome Purification

The microsome fraction comprises a heterogenous set of vesicles 20-200 nm in diameter formed from the endoplasmic reticulum when cells are disrupted. The vesicles are isolated by differential centrifugation and are composed of three structural features: rough vesicles, smooth vesicles and ribosomes. Numerous enzyme activities are associated with the microsomal fraction. Microsomes are defined operationally as the particulate fraction obtained from a tissue homogenate by ultra centrifugation after the nuclear and mitochondrial fractions have been removed by low speed centrifugation. Electron microscopy has shown that microsomes are composed primarily of closed sacs of membrane called vesicles. Most of the vesicles are derived from rough and smooth endoplasmic reticulum (ER). Membrane vesicles derived from the Golgi apparatus, peroxisomes, endosomes, the trans Golgi network, and other intermediate compartments comprise a minor component of microsomes. Liver microsomes contain rough and smooth ER vesicles in a approx. 2:1 ratio, and, in addition to components of the protein secretory pathway, contain a number of proteins involved in lipid/lipoprotein biosynthesis, and drug metabolism. The ER is by far the most abundant membrane in metabolically active cells. About 2-3 mg of microsomal protein can be obtained from liver per gram of wet tissue. As such, microsomes are an ideal preparation in which to study the relationships between enzyme structure, protein-protein and lipid-protein interactions, and the functional properties of membrane bound enzymes. Although many of the most abundant microsomal proteins have been studied extensively, many more remain to be isolated and characterized.

Method:

1. Work on ice during all steps
2. Incubate cells in 30 ml of ice-cold 250 mM phosphate buffer, pH 7.5

Homogenise the cells with an homogenizer without lysing nuclei (contaminates microsomes with genomic DNA). Check under microscope that the nuclei intact.

4. Add 15 ml of ice cold 250 mM phosphate buffer, pH 7.5
7. Centrifuge at 11,000 rpm in an SS34 rotor (14,500×g) for 15 minutes at 4° C.
8. Recover the supernatant Centrifuge again at 11,000 rpm in an SS34 rotor (14,500×g) for 15 minutes at 4° C.

10. Recover the supernatant in a polycarbonate thick-walled tube or 70 Ti rotor
11. Centrifuge at 33,000 rpm in a 70 Ti rotor (105,000×g) for 90 minutes at 4° C. Remove the supernatant
12. Resuspend the pellet in 1 ml of ice-cold 250 mM phosphate buffer/20% glycerol
13. Homogenise with a glass Dounce.
14. Aliquot and store in liquid nitrogen or at −80° C.

9-h) Generation of Inverted Microsomes

After a tissue has been selected for study, the composition of the homogenizing buffer, the method of homogenization, and the time and force of the low speed centrifugation step are the primary variables in the preparation of microsomes. Approximately 10 g of liver per experimental treatment was allowed to thaw in a room temperature homogenization buffer (0.1 M potassium phosphate buffer, pH 7.4, containing 0.125 M potassium chloride and 1.0 mM EDTA). After transfer to 25 ml of chilled homogenization buffer (plus or minus 0.25 M sucrose in the buffer experiment), livers were minced thoroughly with scissors and homogenized with 10 strokes (6, 8, or strokes in the strokes experiment) using a Teflon-glass homogenizer (870 rpm). Strokes were even and steady, lasting approximately 15 s for passage, except for the first two strokes where greater pressure and time were spent on material on the bottom of the glass tube. The tube was submersed in a small bucket of ice and water during all homogenization. The homogenate was diluted to 4 volumes of sample weight (approximately 40 ml). The samples then were centrifuged at 12,000 g (9,000, 10,500, or 12,000 g in the force experiment) in a Sorvall RC-5B with a Sorvall SA-600 rotor for 20 min (Sorvall, Newton, Conn.). The supernatant from the first centrifugation was removed, the mitochondrial pellet was resuspended in 25 ml, and the centrifugation was repeated. The supernatants were combined and centrifuged at 138,000 g in a Sorvall Ultra Pro 80 with a Sorvall T-1270 rotor for 60 min. The upper lipid layer was removed and the cytosolic supernatant collected. The microsomal pellet was resuspended in 0.125 M KCl, 0.1 M Tris (pH 7.4) with three homogenization strokes, and the 138,000 g centrifugation for 60 min was repeated. The microsomal pellet was resuspended in incubation buffer with six strokes and brought to a final volume of 26 ml. Samples were stored at −70° C.

9-i) Reagents Required

Human buffy Coat blood and Ficoll to purify PBMC

Human PE or FITC conjugated for FACS analysis use, for CD86, HLA-DR, CD11c, and CD3.

Intracellular staining kit for measuring secreted cytokine, IFN-γ and IL-4 by T cells MACS magnetic cell isolation kit containing MACS LS columns, MACS separation unit, MACS multi stand and CD4 T cell isolation beads CFSE kit for measuring T cell proliferation in response to the protein or peptide antigen Mitomycin C and recombinant human IL-2, as well as PMA/ionomycin, used as a positive control for T cell proliferation.

9-j) Monocyte to DC Differentiation

Differentiation of monocytes to DC is done in vitro with exogenous IL-4 and GMCSF for 7 days. The resultant cell population is characterised by multicolour staining for cell surface molecules CD11c, CD123, HLA-DR. In general, 90% of the cells in culture are positive for DC markers while 5% are positive for lymphocyte markers, CD3 and CD5.

The DC preparation is pulsed with BCG (Bacille Calmette-Guerin antigens) and TT (tetanus-toxoid), activation of cell surface markers and cytokines secreted and the kinetics of secretion are determined.

DC activation is determined by multicolour cell surface staining for CD11c and CD123 to identify DC and HLA-DR and CD40 as markers for activation. In general, about 75% of antigen-pulsed DC exhibit an activated phenotype, ie, high expression of MHC class II (HLA-DR) and co-stimulatory molecule CD40.

Pro-inflammatory cytokines produced by activates DC are assayed by cytokine arrays. Robust amounts of IL-6, moderate amounts of TNF-α and low amounts of IL-10 were detected in 24 h cultures. No IL-12 was detected, suggesting a polarising effect towards Th2 pathway as expected of a protein antigen. The kinetics of cytokine production was determined at 17 h, 24 h, 92 h and 115 h post antigenic stimulation and the optimal time was 24 h after antigenic stimulation.

DC-lymphocyte conjugate formation for antigen presentation: Antigen-pulsed DC are cultured with autologous T cells for 24 h. Within 24 h after exposure to BCG and TT, DC-lymphocyte conjugates are observed by microscopy. Formation of DC-lymphocytes is photographed and the number of lymphocytes conjugated to a single DC counted. In general, each antigen-pulsed DC is able to bind to a minimum of 25 lymphocytes.

1) DC derived from monocytes
2) Pulsed with antigens (65, 41 and 72)
3) Supernatant collected at 18 hours and assayed for cytokines
4) Cells stained for APC activation markers
5) APC induced antigen specific T-cell proliferation and cytokines monitored.

9-k) Immune Response Test

In animal tests, mice (7 mice in each group) were immunized with proteins 41, 65, 72 subcutaneously. Serum samples of immunized and naïve mice were tested at a dilution of 1:100 on ELISA plates coated with antigens: protein 41, 65, 72, dendroaspin, HSP60, and prevenar. See FIGS. 7 and 8.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A recombinant fusion protein comprising:
   i) a carrier protein;
   ii) a first epitope capable of eliciting an immune response against Apolipoprotein B (ApoB); and
   iii) a second epitope capable of eliciting an immune response against heat-shock protein (HSP), wherein the second epitope consists of the amino acid sequence set forth as SEQ ID NO: 26.

2. A recombinant protein according to claim 1, wherein said first epitope is capable of eliciting an immune response against Apolipoprotein B1 (ApoB1) or Apolipoprotein B2 (ApoB2).

3. A recombinant protein according to claim 2, wherein said first epitope is capable of eliciting an immune response against ApoB1, and comprises the amino acid sequence set forth as SEQ ID NO: 25.

4. A recombinant protein according to claim 2, wherein said first epitope is capable of eliciting an immune response against ApoB1, and consists of the amino acid sequence set forth as SEQ ID NO: 25.

5. A recombinant protein according to claim 1, wherein said HSP is a HSP60.

6. A recombinant protein according to claim 5, wherein said HSP60 is a human HSP60.

7. A recombinant protein according to claim 1, wherein said carrier protein is a dendroaspin scaffold.

8. A recombinant protein according to claim 7, wherein said first epitope is inserted into dendroaspin loop II and said second epitope is inserted into dendroaspin loop III.

9. A recombinant protein according to claim 1, wherein said carrier protein is a keyhole limpet hemocyanin (KLH).

10. An immunogenic composition comprising the recombinant protein according to claim 1 and an immunogenic hydrophobic complex.

11. An immunogenic composition according to claim 10, wherein said immunogenic hydrophobic complex comprises an isolated microsome.

12. An immunogenic composition according to claim 10, wherein said immunogenic hydrophobic complex comprises an MHC protein.

13. An immunogenic composition according to claim 11, wherein the microsome is an inverted microsome.

14. The immunogenic composition of claim 10, further comprising an adjuvant.

15. A method of eliciting an anti-atheroma response in a mammal, comprising administering to the mammal: the recombinant protein according to claim 1;
   an immunogenic composition comprising the recombinant protein according to claim 1 and an immunogenic hydrophobic complex.

* * * * *